US012589144B2

(12) United States Patent  
Raychaudhuri

(10) Patent No.: US 12,589,144 B2  
(45) Date of Patent: Mar. 31, 2026

(54) COMBINED NOROVIRUS AND ROTAVIRUS VACCINE COMPOSITION AND METHODS OF PREPARATION

(71) Applicant: BHARAT BIOTECH INTERNATIONAL LIMITED, Hyderabad (IN)

(72) Inventor: Mithu Raychaudhuri, Hyderabad (IN)

(73) Assignee: BHARAT BIOTECH INTERNATIONAL LIMITED, Hyderabad (IN)

( * ) Notice: Subject to any disclaimer, the term of this patent is extended or adjusted under 35 U.S.C. 154(b) by 938 days.

(21) Appl. No.: 17/791,076

(22) PCT Filed: Jan. 6, 2021

(86) PCT No.: PCT/IN2021/050018

§ 371 (c)(1),  
(2) Date: Jul. 6, 2022

(87) PCT Pub. No.: WO2021/140524

PCT Pub. Date: Jul. 15, 2021

(65) Prior Publication Data

US 2023/0285534 A1     Sep. 14, 2023

(30) Foreign Application Priority Data

Jan. 8, 2020     (IN) .............................. 202041000777

(51) Int. Cl.  
*A61K 39/12*     (2006.01)  
*A61K 45/06*     (2006.01)  
(Continued)

(52) U.S. Cl.  
CPC .............. *A61K 39/12* (2013.01); *A61K 45/06* (2013.01); *A61P 31/12* (2018.01); *A61K 39/295* (2013.01);  
(Continued)

(58) Field of Classification Search  
None  
See application file for complete search history.

(56) References Cited

U.S. PATENT DOCUMENTS 5,147,639 A * 9/1992 Welter ............. G01N 33/56983  
435/238  
2010/0209455 A1 8/2010 Jiang et al.  
(Continued)

FOREIGN PATENT DOCUMENTS

WO     WO 2009/032913     * 3/2009  
WO     2012/006293     1/2012  
WO     WO 2012/049366     * 4/2012

OTHER PUBLICATIONS

Fernandez et al. (PLoS One. 2013; 8 (2): e56417).*  
(Continued)

*Primary Examiner* — Shanon A. Foley  
(74) *Attorney, Agent, or Firm* — Wenderoth, Lind & Ponack, L.L.P.

(57) ABSTRACT

The present invention relates to vaccine composition comprising inactivated rotavirus antigen, methods of inactivation and preparation of vaccine composition thereof. The present invention also discloses a combination vaccine comprising inactivated rotavirus antigen and norovirus antigen, and vaccine preparations thereof.

40 Claims, 15 Drawing Sheets

Specification includes a Sequence Listing.

(51) Int. Cl.

*A61P 31/12* (2006.01)
*A61K 39/00* (2006.01)
*A61K 39/295* (2006.01)

(52) U.S. Cl.

CPC ................. *A61K 2039/5252* (2013.01); *A61K 2039/5258* (2013.01); *A61K 2039/55511* (2013.01)

(56) References Cited

U.S. PATENT DOCUMENTS

| | | | |
|---|---|---|---|
| 2010/0266636 A1* | 10/2010 | Richardson | A61P 31/14 424/216.1 |
| 2016/0222066 A1* | 8/2016 | Settembre | A61K 39/12 |
| 2018/0028626 A1* | 2/2018 | Slos | A61K 38/193 |
| 2018/0141978 A1* | 5/2018 | Ge | A61P 1/12 |
| 2023/0285534 A1* | 9/2023 | Raychaudhuri | A61P 31/14 |

OTHER PUBLICATIONS

Huhti et al. (Archives of Virology. 2010; 155: 1855-1858).*
International Search Report and Written Opinion issued Apr. 20, 2021 in International (PCT) Application No. PCT/IN2021/050018.
Blazevic, Vesna et al., "Norovirus VLPs and rotavirus VP6 protein as combined vaccine for childhood gastroenteritis", Vaccine, 2011, vol. 29, pp. 8126-8133.

* cited by examiner

SEQUENCE LISTING

<160> NUMBER OF SEQ ID NOS: 2

<210> SEQ ID NO 1
<211> LENGTH: 1623
<212> TYPE: DNA
<213> ORGANISM: Norovirus sp.
<220> FEATURE:
<221> NAME/KEY: misc_feature
<223> OTHER INFORMATION: VP1 sequence from a single isolate

<400> SEQUENCE: 1
atgaagatgg cttctagtga cgccaaccca tctgatggat ctgcagccaa cttggtccca    60

-continued

```
gaggtcaaca atgaggttat ggctctggag cctgttgttg gtgccgccat tgccgcacct        120
gtagccggtc aacaaaatgt aattgaccca tggattagaa acaattttgt tcaagcccct        180
ggtggagagt ttacagtttc acctagaaac gctccaggtg aaattttgtg gtctgcccct        240
ttgggccctg atttgaatcc ttacttgtca catttggcca gaatgtacaa tggttatgca        300
ggtggttttg aagtccaggt tattttggcc ggaaacgcct tcaccgccgg aaaggtcatt        360
tttgcagcag tcccaccaaa ttttccaact gaaggtttgt caccttctca ggtcactatg        420
ttccctcata ttgtagtaga tgttaggcaa ttggaacctg tgttgattcc tttgccagat        480
gttaggaata atttctatca ttacaatcaa tcaaatgacc caaccattaa gttgattgca        540
atgttgtata caccattgag ggctaataat gctggagatg atgtcttcac agtttcttgc        600
agagttttga ccagaccatc ccctgatttt gatttcattt ttttggtgcc acctacagtt        660
gagtcaagaa ctaaaccatt ctctgtccca gttttgactg ttgaggagat gaccaattca        720
agattcccaa ttcctttgga aaagttgttc accggtcctt caagtgcctt tgttgtccaa        780
ccacaaaacg gtaggtgcac cactgatgga gtgttgttgg aaccaccca attgtctcct        840 gtcaacatct gcaccttcag aggagatgtc acccatatca caggttctag aaactacaca        900
atgaatttgg cttctcaaaa ttggaacaat tatgacccaa cagaagaaat cccagcccct        960
ttgggaactc cagattttgt cggtaagatt caaggtgtct tgacccaaac cacaaggaca        1020
gacggatcaa caaggggtca caagctaca gtgtacactg gttcagccga ctttgctcca        1080
aaattgggta gagttcaatt tgaaactgac acagaccatg attttgaagc taaccaaaac        1140
acaaagttca ccccagtcgg tgtcatccaa gatggttcta ccacccacag aaatgaacct        1200
caacagtggg tcttgccatc ttactcaggt agaaatactc ataatgtgca tttggcccct        1260
gctgttgccc ctactttttcc tggtgagcaa ttgttgttct tcagatcaac catgcctgga        1320
tgctctggtt accctaacat ggatttggac tgtttgttgc ctcaggaatg ggtccagtac        1380
ttctaccaag aggcagcccc agcacaatct gatgtggctt tgttgagatt tgtgaatcca        1440
gacacaggta gggttttgtt tgagtgtaag ttgcataaat caggatatgt tacagtcgct        1500
cacactggtc aacatgattt ggttatccct ccaaatggtt attttaggtt tgattcttgg        1560
gtaaaccagt tctacacgtt ggcccctatg ggaaatggaa ccggtagaag aagggttgtt        1620
taa                                                                      1623
```

```
<210> SEQ ID NO 2
<211> LENGTH: 1623
<212> TYPE: DNA
<213> ORGANISM: Norovirus sp.
<220> FEATURE:
<221> NAME/KEY: misc_feature
<223> OTHER INFORMATION: VP1 sequence from a chimera from different
      isolates of GII.4

<400> SEQUENCE: 2
```

```
atgaagatgg cttctagtga cgccaaccca tctgatggat ctgcagccaa cttggtccca         60
gaggtcaaca atgaggttat ggctctggag cctgttgttg gtgccgccat tgccgcacct        120
gtagccggtc aacaaaatgt aattgaccca tggattagaa acaattttgt tcaagcccct        180
ggtggagagt ttacagtttc acctagaaac gctccaggtg aaattttgtg gtctgcccct        240
ttgggccctg atttgaatcc ttacttgtca catttggcca gaatgtacaa tggttatgca        300
ggtggttttg aagtccaggt tattttggcc ggaaacgcct tcaccgccgg aaaggtcatt        360
```

-continued

```
tttgcagcag tcccaccaaa ttttccaact gaaggtttgt caccttctca ggtcactatg    420
ttccctcata ttgtagtaga tgttaggcaa ttggaacctg tgttgattcc tttgccagat    480
gttaggaata atttctatca ttacaatcaa tcaaatgacc caaccattaa gttgattgca    540
atgttgtata caccattgag ggctaataat gctggagatg atgtcttcac agtttcttgc    600
agagttttga ccagaccatc ccctgatttt gatttcattt ttttggtgcc acctacagtt    660
gagtcaagaa ctaaaccatt ctctgtccca gttttgactg ttgaggagat gaccaattca    720
agattcccaa ttcctttgga aaagttgttc accggtcctt caagtgcctt tgttgtccaa    780
ccacaaaacg gtaggtgcac cactgatgga gtgttgttgg gaaccaccca attgtctcct    840
gtcaacatct gcaccttcag aggagatgtc acccatatca caggttctag aaactacaca    900
atgaatttgg cttctcaaaa ttggaacaat tatgacccaa cagaagaaat cccagcccct    960
ttgggaactc cagattttgt cggtaagatt caaggtgtct tgacccaaac cacaaggaca   1020
gacggatcaa caaggggtca caaagctaca gtgtacactg gttcagccga ctttgctcca   1080
aaattgggta gagttcaatt tgaaactgac acagaccatg attttgaagc taaccaaaac   1140
acaaagttca ccccagtcgg tgtcatccaa gatggtaatt ctgctcacag aaatgaacct   1200
caacagtggg tcttgccaaa ttactcaggt agaactggtc ataatgtgca tttggcccct   1260
gctgttgccc ctacttttcc tggtgagcaa ttgttgttct tcagatcaac catgcctgga   1320
tgctctggtt accctaacat ggatttggac tgtttgttgc ctcaggaatg ggtccagtac   1380
ttctaccaag aggcagcccc agcacaatct gatgtggctt tgttgagatt tgtgaatcca   1440
gacacaggta gggtttttgtt tgagtgtaag ttgcataaat caggatatgt tacagtcgct   1500
cacactggtc aacatgattt ggttatccct ccaaatggtt attttaggtt tgattcttgg   1560
gtaaaccagt tctacacgtt ggcccctatg ggaaatggaa ccggtagaag aagggttgtt   1620
taa                                                                 1623
```

COMBINED NOROVIRUS AND ROTAVIRUS VACCINE COMPOSITION AND METHODS OF PREPARATION

SEQUENCE LISTING

A sequence listing in electronic (ASCII text file) format is filed with this application and incorporated herein by reference. The name of the ASCII text file is "2022_1268A_ST25.txt"; the file was created on Dec. 9, 2022; the size of the file is 5,053 bytes.

RELATED PATENT APPLICATION

This application claims the priority to and benefit of Indian Patent Application No. 202041000777 filed on Jan. 8, 2020; the disclosure of which are incorporated herein by reference.

FIELD OF THE INVENTION

The present invention relates to the field of inactivation of Rotavirus by different methods and preparation of inactivated rotavirus vaccine compositions that elicit strong immune response.

The present invention also discloses a combination vaccine for prophylaxis and treatment against any genotype or antigenic variants of rotavirus and norovirus and the methods of inactivation and vaccine preparations thereof.

BACKGROUND OF THE INVENTION

Rotavirus (RV) is the most common cause of severe diarrhoea in infants and children below 5 years of age. Although the disease can be managed by palliative medical care, in 2013, about 215,000 children died worldwide due to rotavirus infection. Approximately half of these deaths happened in four countries (India, Pakistan, Nigeria and Democratic Republic of Congo). Four oral, live, attenuated rotavirus vaccines, Rotarix® (derived from a single strain of human rotavirus, manufactured by GlaxoSmithKline plc); RotaTeq® (a pentavalent reassorted bovine-human rotavirus, manufactured by Merck Sharp & Dohme Corp.); Rotavac® (naturally attenuated human-bovine reassorted neonatal strain G9P11, also called 116E, manufactured by Bharat Biotech International Limited (the Applicant)); and Rota-Siil® (bovine-human reassortant with human G1, G2, G3, G4 and G9 in bovine UK G6P backbone, manufactured by Serum Institute of India Limited) are available internationally and are WHO prequalified. Immunization with oral rotavirus vaccine (ORV) has dramatically reduced hospitalization in many developed countries and WHO recommends that rotavirus vaccines should be included in all national immunization programmes. However, the vaccines are least effective in low income countries where the disease burden and mortality are high. The reason is not fully understood but could be attributed to several factors such as high titer of maternal antibodies, poor nutritional status of the infants, gut microbiota etc. Similar observations were made with other live oral vaccines e.g. polio, cholera, typhoid. Parenteral vaccines have been successful in overcoming this problem. Apart from low efficacy, a rare risk of intussusception is also associated with ORV. The concerns regarding safety and efficacy of ORV demands an alternative approach for parenteral vaccination using inactivated rotavirus vaccine (IRV). Rotavirus is a double stranded RNA virus of family Reoviridae. There are 9 species represented as strains A, B, C, D, E, F, G, H and I, among them Rotavirus A accounts for >90% of human infection. The virus gets transmitted by fecal-oral route. It damages the enterocytes and results in gastroenteritis. Rotavirus genome consists of 11 segments of double stranded RNA held in the inner core of the three-layered virus. The three layers consist of a core protein VP2 bound to dsRNA, an inner capsid protein VP6, and an outer capsid glycoprotein VP7 with hemagglutinin spike protein VP4. The major capsid protein VP6 determines viral group specificity and is the most conserved, immunogenic, and abundant rotavirus protein. The outer capsid proteins VP7 and VP4 contain neutralizing epitopes and induce protective immunity on the basis of neutralizing antibodies.

After rotavirus, norovirus is the most common cause of viral gastroenteritis in children. Noroviruses (NV) are members of the family Caliciviridae causing about 685 million cases of disease and 200,000 deaths globally a year.

A norovirus genome consists of a single stranded RNA of about 7.6 kb that is organized into three open reading frames (ORF 1-3). ORF1 codes for RNA-dependent RNA polymerase which are similar to other ssRNA viruses; ORF2 encodes major capsid protein VP1 and ORF3 codes small structural protein VP2. Most NVs affecting humans belong to two genogroups (GI and GII), and these two genogroups are divided into several genotypes. Among these genotypes, GII-4 has been shown to be primarily responsible for the majority of cases.

A unique feature of the capsid VP1 protein is its ability to self-assemble into the empty virus-like particles (VLPs). These VLPs are morphologically and antigenically similar to the native NV. Norovirus VLPs are widely used as a source of antigen in diagnostic serological assays, as well as for development of candidate vaccines against noroviruses. Although the receptor/s for norovirus binding and entry is/are not completely elucidated, it has been found that NV recognize human histo-blood group antigens (HBGAs) as receptors. Among the HBGAs, the most commonly encountered blood groups are ABO (ABH) and Lewis. These complex carbohydrates are found on the red blood cells and mucosal epithelial cells or as free antigens in biological fluids. Further, it has been found that the recognition of HBGAs by NV is strain-specific, and several distinct receptor binding patterns have been identified.

For norovirus, a live vaccine is not an option, because noroviruses cannot be cultivated in a cell culture. Therefore, the candidate vaccines for norovirus are likely to be either VLP vaccines or soluble antigen vaccines. Given the severity of rotavirus and norovirus infections and deficiencies in the currently available vaccines, there is a need for both non-live norovirus and rotavirus vaccines, especially for the prevention of acute gastroenteritis in childhood. A vaccine consisting of whole inactivated RV and norovirus VLPs represents a viable strategy to immunize against NV and RV infection.

No vaccine is available in the market that provides for efficient inactivation of Rotavirus.

Further, there is no single vaccine that provides protection against Rotavirus and Norovirus. Therefore, the present invention provides the solution to the problem by disclosing Rotavirus inactivation method and monovalent formulation of inactivated rotavirus vaccine, as well as bivalent vaccine compositions comprising inactivated Rotavirus antigen and Norovirus antigen (VLPs).

OBJECTS OF THE INVENTION

The main object of this invention is to provide stable immunogenic compositions for prophylaxis and treatment of Rotavirus infections.

Another object of the invention is to provide methods for rotavirus inactivation.

Another object of the invention is to provide methods for the preparation of inactivated rotavirus vaccine and purification of inactivated rotavirus bulk antigen.

One more object of the invention is to provide methods for rotavirus inactivation by chemical means with formalin and hydrogen peroxide.

Another object of the invention is to provide methods for rotavirus inactivation by physical means such as heat and ultraviolet light.

Yet another object of the invention is to provide methods for rotavirus inactivation by a combination of physical and chemical means with heat and formalin.

Another object of the invention is to provide methods for purification of live and/or inactivated rotavirus bulk antigen.

Another object of the invention is to provide kinetics of immune response to single dose, two and three doses of formalin, heat, hydrogen peroxide, heat with formalin inactivated rotavirus vaccines in animals.

One more object of the invention is to provide a comparison of antigen recovery of inactivated rotavirus compared to live virus when inactivated before and after purification.

Yet another object is to evaluate the antigenic recovery of rotavirus inactivated in different buffers which includes but not limited to phosphate buffer saline (PBS), Tris-NaCl—CaCl2 (TNC, pH: 7.4), Hank's Balanced Salt Solution (HBSS).

A further object of the invention is to provide methods for formulations of rotavirus antigen with different adjuvants and estimation of immune response to the formulations in animals.

Another object of the invention is to provide methods for formulation of rotavirus antigen with norovirus VLPs to prevent and treatment of rotavirus and norovirus infection in children in one single combined vaccine.

Yet another object is estimation of immune response and immune interference of bivalent combination vaccine of inactivated rotavirus antigen and norovirus VLP.

SUMMARY OF THE INVENTION

One aspect of the invention is to provide a stable immunogenic composition for prophylaxis and eliciting an immune response against rotavirus and norovirus infections in a single combined vaccine.

In some embodiment, there is provided a bivalent vaccine formulation comprising rotavirus antigen with norovirus VLPs for prevention and treatment of rotavirus and norovirus infection in children in one single combined vaccine. In some other embodiment, there is provided method for preparing vaccine formulation comprising rotavirus antigen and norovirus VLPs.

Another aspect of the present invention is to provide a vaccine composition wherein the norovirus antigen is virus like particle (VLP) and is applicable to any genotype/strains/genetic variants of norovirus.

Norovirus antigens present in this invention include capsid proteins that self-assemble into VLPs and antigenically mimic the whole virus. Norovirus antigens is derived from any norovirus genotype of genogroup GI and GII and more particularly GII.4 VLP.

Norovirus antigen in this invention is monovalent or bivalent or trivalent belonging to the same genogroup or different genogroup. In a specific example, norovirus VLPs are derived from either expression of only VP1 protein or by co-expression of VP1 and VP2 in a suitable host.

The norovirus antigen is derived from sequence from a single isolate of norovirus or a chimera representing different isolate from the same genotype (GII.4).

VP1 gene from GII.4 is synthesized and cloned into a suitable vector for expression of the protein. The expression system for norovirus VLPs production is selected from, but not limited to yeast cells, bacterial cells, insect cells and mammalian cells and particularly the expression system for norovirus VLPs production is yeast and more particularly *Pichia pastoris*. The VP1 protein is expressed and secreted in the medium where they self-assemble into VLPs.

The VLPs were concentrated and purified from the cell supernatant by methods selected from i) ultrafiltration through 100 kD-1000 kD membrane ii) ultracentrifugation and density gradient centrifugation iii) column chromatography such as gel filtration, ion exchange chromatography, hydrophobic interaction chromatography, affinity matrix chromatography or a combination thereof.

In some embodiment, there is provided a liquid vaccine formulation comprising of: i) purified norovirus VLPs ii) 50 mM phosphate buffer, pH 7, is stable for 6 months at 4° C. The vaccine antigen at concentrations ranging from 0.1 μg to 50 μg is formulated with or without an adjuvant. The adjuvant is selected from the group consisting of i) aluminum salts comprising aluminum hydroxide, aluminum phosphate, aluminum sulphate phosphate; ii) inulin; iii) algammulin which is a combination of inulin and aluminium hydroxide; iv) monophosphoryl lipid A (MPLA); v) CpG oligonucleotide; vi) aluminum hydroxide with MPLA or a combination thereof.

The said vaccine composition elicited protective immune response against norovirus in mammals. The said vaccine composition elicited both Th1 and Th2 immune response against norovirus. The vaccine composition is administered as single dose, two doses or more than two doses.

The antigenic property of the VLPs in the present invention is characterized by in vitro binding capacity of purified VLPs against salivary HBGAs and/or the mucin from porcine stomach Type III. Potency of norovirus VLPs either alone or in combination with rotavirus antigen is evaluated in Balb/C mice in a dose ranging from 0.1 μg to 40 μg with or without adjuvants. Immunogenicity of the vaccine formulation is evaluated by in vitro Mucin-VLPs binding blockade assay and by induction of norovirus specific serum IgG and IgA. The VLPs are found to be highly efficacious in inducing immune response in animal model. The efficacy of the bi-valent combination is evaluated separately for each component and no immune-interference is observed.

Another aspect of the present invention is to provide a vaccine composition wherein the vaccine antigen is selected from rotavirus and norovirus antigen being formulated with or without adjuvants.

Yet another aspect of present invention is to provide vaccine compositions against rotavirus that can be administered parenterally. The parenteral vaccine against rotavirus uses inactivated rotavirus preparations, alone or in combination with adjuvants. The methods described in the present invention are applicable to any genotype/strains/genetic variants of rotavirus that infect human or animal.

In some embodiment, there is provided a vaccine formulation comprising rotavirus antigen and one or more adjuvant, method of preparation thereof and estimation of immune response to the formulation in animals. In some embodiment, there is provided a stable immunogenic composition for prophylaxis and treatment of Rotavirus infections. In some embodiment, there is provided a method for rotavirus inactivation and preparation of vaccine composition thereof.

The rotavirus in present invention is a human or animal rotavirus of group A, B, C, D, E, F and G. The rotavirus strain is more particularly a live attenuated human rotavirus. The said rotavirus antigen in the formulation is purified and inactivated rotavirus. The inactivation is confirmed by a method with a sensitivity to detect 0.1 FFU/ml live rotavirus.

The said rotavirus antigen is inactivated by heat either before or after purification of the virus, wherein the said virus is incubated at a temperature ranging from 42° C.-60° C. wherein incubation time range is from 30 minutes to 10 days to render the virus incapable of infection and replication.

The said virus antigen is inactivated by chemical means either before or after purification of the virus. The purified virus is inactivated by chemical inactivating agent selected from i) Formalin at a concentration ranging from 1:1000 (formalin:virus, v/v) to 1:4000 (formalin:virus, v/v) at temperature 25° C.-37° C. for 3-10 days; ii) hydrogen peroxide at a concentration ranging from 0.05% to 3% at 4° C. to 25° C. for a period of 4-48 hours.

The virus is also inactivated with a combination of heat and chemicals either before or after purification of the virus; wherein the temperature ranging from 40° C.-55° C. in presence of formalin at a concentration ranges from 1:5000 (formalin:virus, v/v) to 1:50000 (formalin:virus, v/v) for a period of 2-24 hrs.

In another embodiment, the virus is inactivated first and then purified. The starting material of rotavirus particles used for inactivation can be double-layer rotavirus particles, triple-layer rotavirus particles, or a mixture of both.

The structure of the inactivated rotavirus is substantially intact when compared to its live counterpart. The inactivated rotavirus preparation is characterized by an amount of substantially intact viral proteins VP1, VP2 and VP6 which is substantially similar to the amount of live viral proteins VP1, VP2 and VP6 present in the starting preparation.

Rotavirus is grown in Vero cells and the virus is concentrated and purified by methods selected from i) ultrafiltration through 100 kD-1000 kD membrane ii) ultracentrifugation and density gradient centrifugation iii) column chromatography such as gel filtration, ion exchange chromatography, hydrophobic interaction chromatography, affinity matrix chromatography or a combination thereof.

The cell culture medium can be filtered and concentrated before purification. The purified virus is then resuspended in a buffer having an osmolality in the range of about 200-500 mOsm (milli-osmoles), comprising at least one salt of a divalent cation with a concentration in the range of about 1 mM-15 mM, and a sugar and/or sugar alcohol in the range of about 1-20% w/v.

In some embodiment, there is provided a stable liquid vaccine formulation comprising of: i) purified and inactivated rotavirus antigen ii) TNC buffer 10 mM Tris, 140 mM NaCl, 10 mM CaCl$_2$ iii) Sugar concentration in the range of 0.1% to 10%, wherein the sugar is selected from lactose, maltose, sucrose, glucose, trehalose, sorbitol or a combination thereof. The said liquid formulation is stable at –20° C. for 8 months. The vaccine antigen at concentrations ranging from 0.1 µg to 100 µg is formulated with or without an adjuvant. wherein the adjuvant is selected from the group consisting of i) aluminum salts comprising aluminum hydroxide, aluminum phosphate, aluminum sulphate phosphate; ii) inulin; iii) algammulin which is a combination of inulin and aluminium hydroxide; iv) monophosphoryl lipid A (MPLA); v) CpG oligonucleotide; vi) aluminum hydroxide with MPL.

The said vaccine composition elicited protective immune response against rotavirus in mammals. The said vaccine composition elicited both Th1 and Th2 immune response against rotavirus. The vaccine composition is administered as single dose, two doses or more than two doses.

The vaccine is formulated either in a pharmaceutically accepted buffer or in a dry lyophilized form which can be reconstituted with a suitable solvent before administration. The stable formulation is suitable for intramuscular/intradermal/subcutaneous/intravenous administration in a human host.

Potency of the rotavirus vaccine inactivated by different methods has been tested in suitable animal model in doses ranging from 0.2 µg to 40 µg. The efficacy of the vaccine formulation is evaluated by virus neutralization test as well as by the level of rotavirus specific serum IgG and IgA. A high rate of seroconversion and protective antibodies against the virus is observed in mice, that were administered with the formulation comprising inactivated rotavirus prepared by different methods. The best method of inactivation is selected based on the immune response in animals. Presence of adjuvants increased the level of immune response. Inactivated rotavirus antigen is also co-formulated with norovirus VLPs to prepare a bi-valent vaccine formulation for parenteral administration in humans.

Another aspect of the present invention is to provide a method for preparation of a combination vaccine against rotavirus and norovirus, wherein norovirus antigen is present in the formulation at a concentration ranges from 0.10 µg up to 100 µg per dose and rotavirus antigen is present in the formulation at a concentration ranges from 0.10 µg up to 50 µg per dose. The said vaccine is formulated with or without an adjuvant. The adjuvant is selected from the group consisting of i) aluminum salts comprising aluminum hydroxide, aluminum phosphate, aluminum sulphate phosphate; ii) inulin; iii) algammulin which is a combination of inulin and aluminium hydroxide; iv) monophosphoryl lipid A (MPLA); v) CpG oligonucleotide; vi) aluminum hydroxide with MPL. The said vaccine composition is administered as single dose, two doses or more than two doses.

In some embodiment, there is provided a composition comprising rotavirus and norovirus antigens in a combination vaccine that elicits protective immune response in mammals against each of the viruses without immune-interference.

Yet another aspect of the present invention is to provide a method of eliciting a protective immune response in mammals including humans comprising administering the said vaccine composition by any route comprising intradermal, subcutaneous, intramuscular, intravenous, oral and intranasal.

(a) Pooled serum samples from 5 mice vaccinated with different formulation of norovirus vaccine twice I.M. were tested for IgG subclasses, IgG1 and IgG2a, respectively, by ELISA as described in the text. Serum specimen from each group was tested at an initial dilution of 1:100. Pre-bleed serum specimens and placebo samples at all time points had no detectable antibody at this dilution, a value of 20 was assigned.

(b) IgG2a:IgG1 ratio of final bleed (42 day) was calculated from antibody levels detected in (a).

Figure 13:
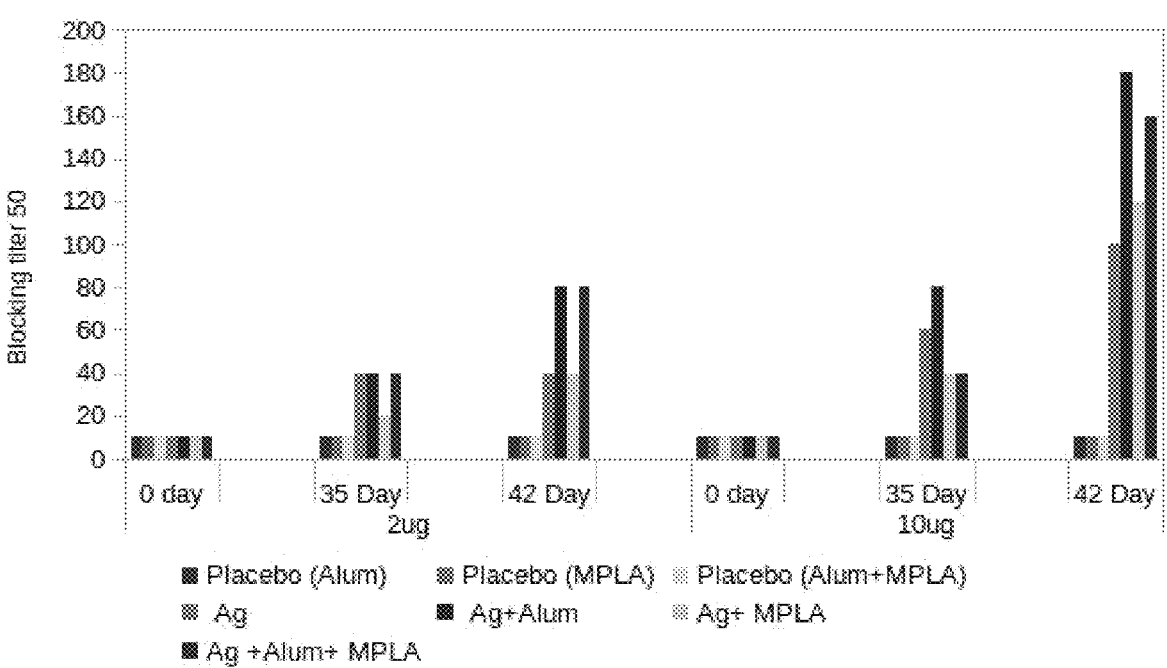

FIG. 13: Surrogate neutralization assay for Norovirus. Norovirus VPLs are known to bind to Pig Gastric Mucin Type III (PGM). Norovirus VLPs are incubated with the sera from the immunized animals and neutralization titer or blocking titer 50 was determined based on the serum dilution at which the percent of binding was <=50% compared to untreated VLPs. The blocking antibody titer for VLP- PGM binding was determined with pooled sera from each group of mice by method described in the text. Sera was tested at an initial dilution of 1:20 and pre-bleed and placebo samples at all time points had no VLP binding blocking activity at this dilution and a value of 10 was used for representation.

Figure 14:
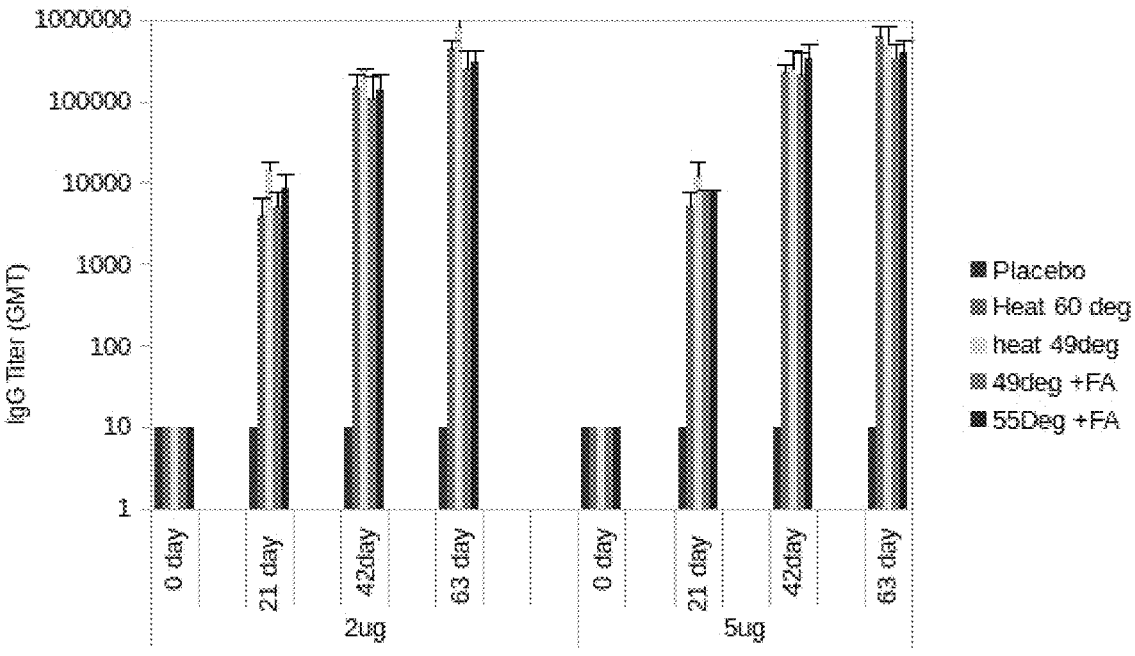

FIG. 14: IgG response to inactivated rotavirus antigens (IRV). Antigens are inactivated by different methods and mice were vaccinated I.M. thrice with 2 μg or 5 μg of antigen (described in Table 8). Blood was collected and sera at different time point after vaccination was tested for IgG antibody titer by ELISA described in the text. Each serum specimen was tested at an initial dilution of 1:100. Pre-bleed serum specimens and placebo samples at all timepoints had no detectable antibody at this dilution, a value of 10 was used for determining geometric mean titers and illustration. Antibody titers are expressed as the geometric means for each group (n=5 or 6). Error bars represent standard deviation.

Figure 15:
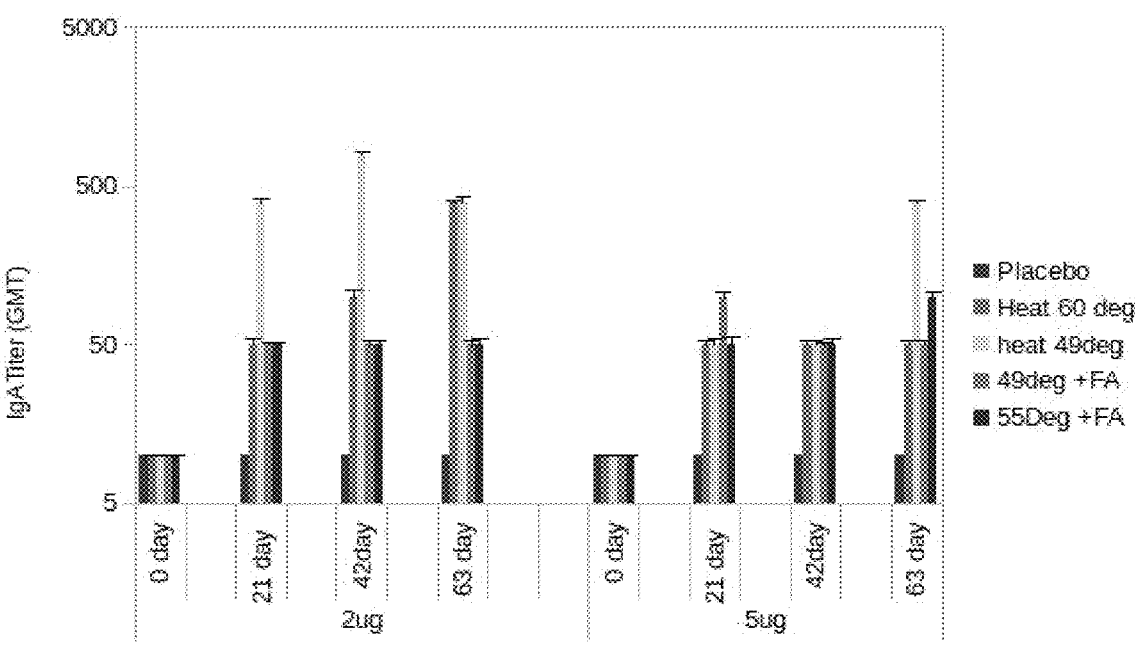

FIG. 15: IgA response to inactivated rotavirus antigens. Mice were vaccinated I.M. thrice with 2 μg or 5 μg of rotavirus antigen inactivated by different methods. IgA antibody titer was measured at different time point after vaccination by ELISA described in the text. Each serum specimen was tested at an initial dilution of 1:100. Pre-bleed serum specimens and placebo samples at all timepoints had no detectable antibody at this dilution, a value of 10 was used for determining geometric mean titers and illustration. Antibody titers are expressed as the geometric means for each group (n=5 or 6). Error bars represent standard deviation.

Figure 16:
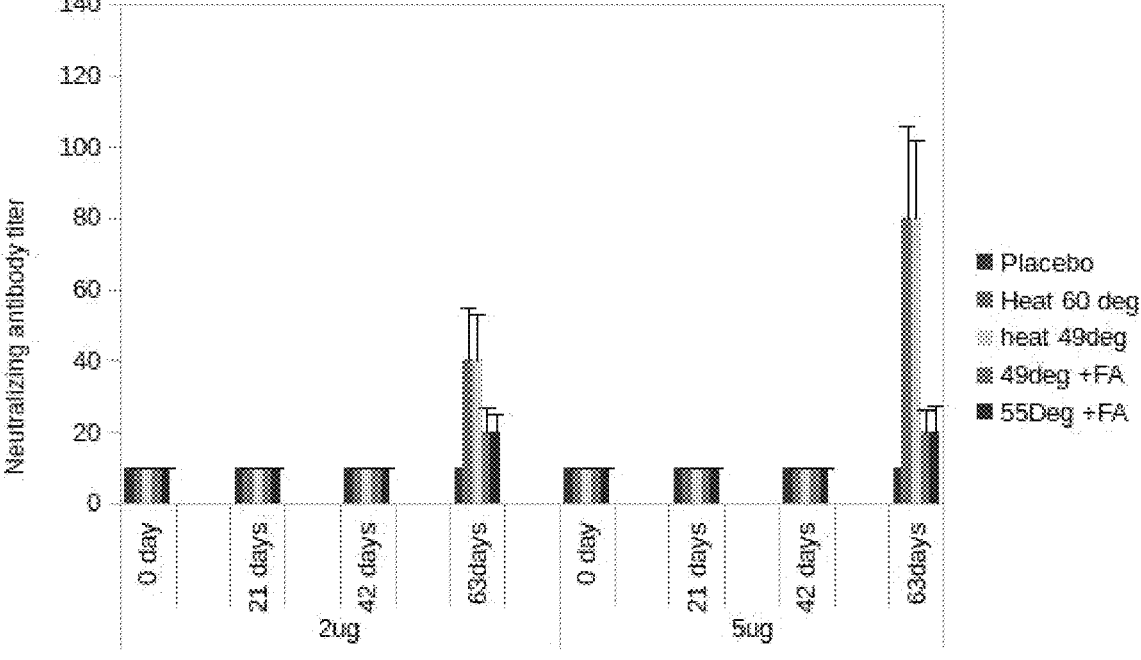

FIG. 16: Neutralizing antibody titer at different time point in different vaccine formulation group was measured by microneutralization assay described in text. Serum sample from each mice was tested at an initial dilution of 1:20. Antibody titers are expressed as the geometric means for each group (n=5 or 6). Error bars represent standard deviation.

Figure 17:
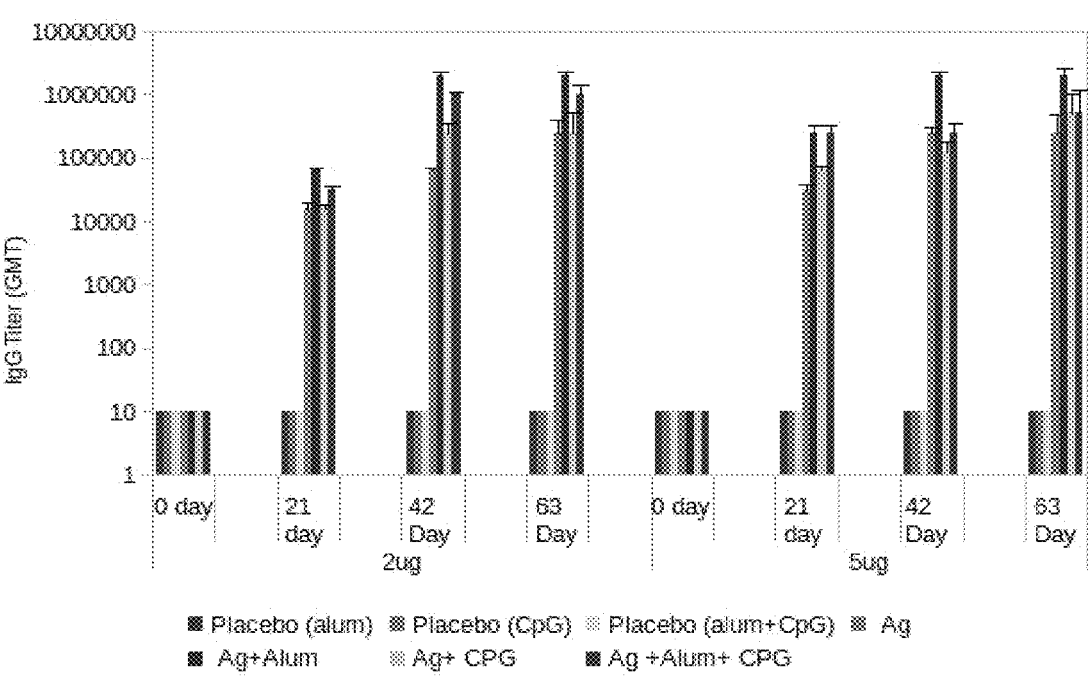

FIG. 17: IgG response to different vaccine formulation of inactivated rotavirus antigen where the inactivation was carried out at 49° C. for four days. Mice were vaccinated I.M. thrice at three weeks interval with different vaccine formulation described in Table-9 in the text. Blood was collected and sera at different time point after vaccination was tested for IgG antibody titer by ELISA described in text. Each serum specimen was tested at an initial dilution of 1:100. Pre-bleed serum specimens and placebo samples at all timepoints had no detectable antibody at this dilution, a value of 10 was used for determining geometric mean titers and illustration. Antibody titers are expressed as the geometric means for each group (n=5 or 6). Error bars represent standard deviation.

Figure 18:
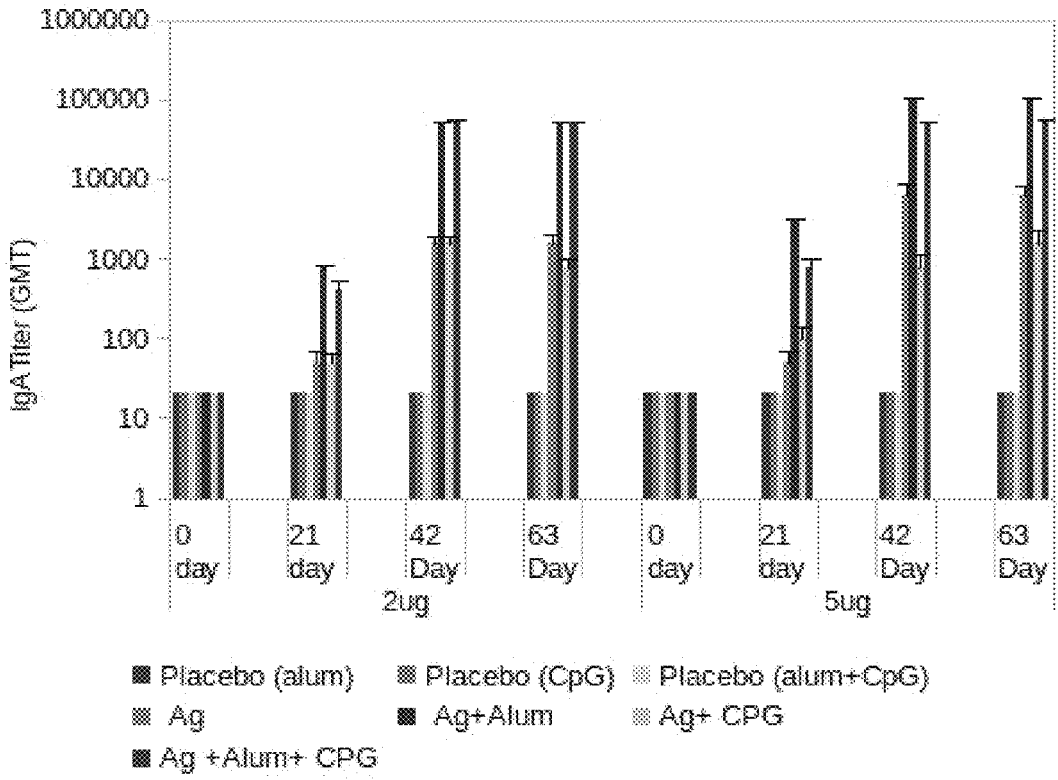

FIG. 18: IgA response to different vaccine formulation described in Table-9 in the text was measured by ELISA. Mice were vaccinated I.M. thrice at three weeks interval with different vaccine formulation. Blood was collected and sera at different time point after vaccination was tested for IgA antibody titer. Each serum specimen was tested at an initial dilution of 1:100. Pre-bleed serum specimens and placebo samples at all time points had no detectable antibody at this dilution, a value of 10 was used for determining geometric mean titers and illustration. Antibody titers are expressed as the geometric means for each group (n=5 or 6). Error bars represent standard deviation.

Figure 19:
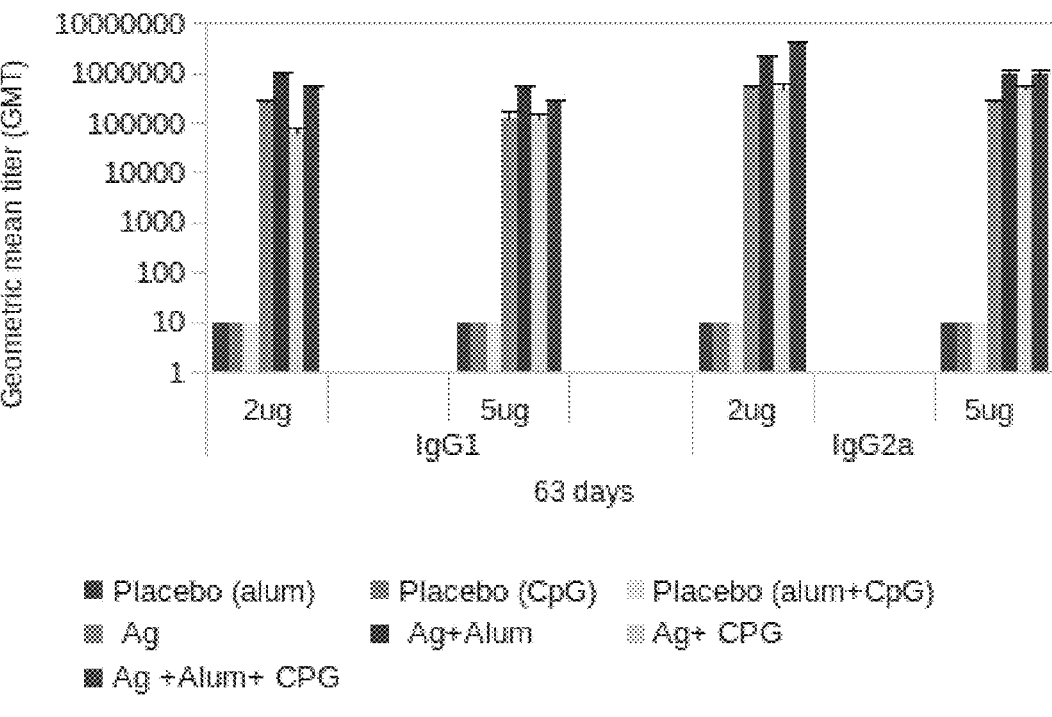
Figure 19:
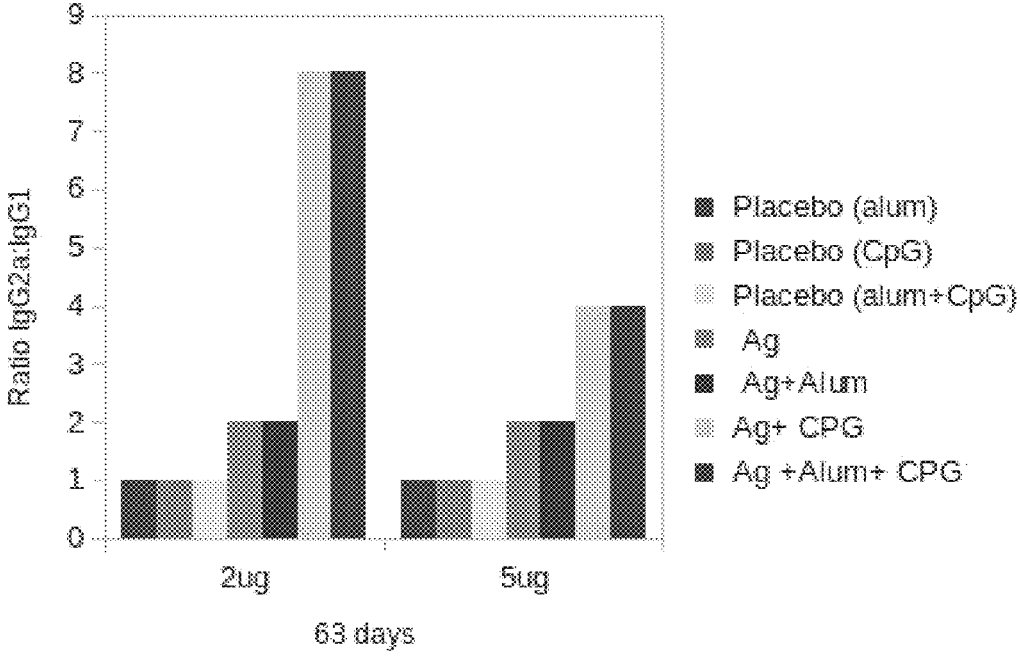

FIG. 19: Different formulation of IRV vaccination leads to elevated levels of rotavirus-specific IgG subclass.

(a) Sera of mice from study endpoint (day 63) were tested for IgG 1 and IgG 2a respectively, by ELISA as described in the text. Each serum specimen was tested at an initial dilution of 1:100. Placebo samples had no detectable antibody at this dilution, a value of 10 was used for determining geometric mean titers of each group (5 mice per group) and error bar represents standard deviation.

(b) IgG 2a:IgG 1 ratio was calculated from antibody levels detected in (a).

Figure 20:
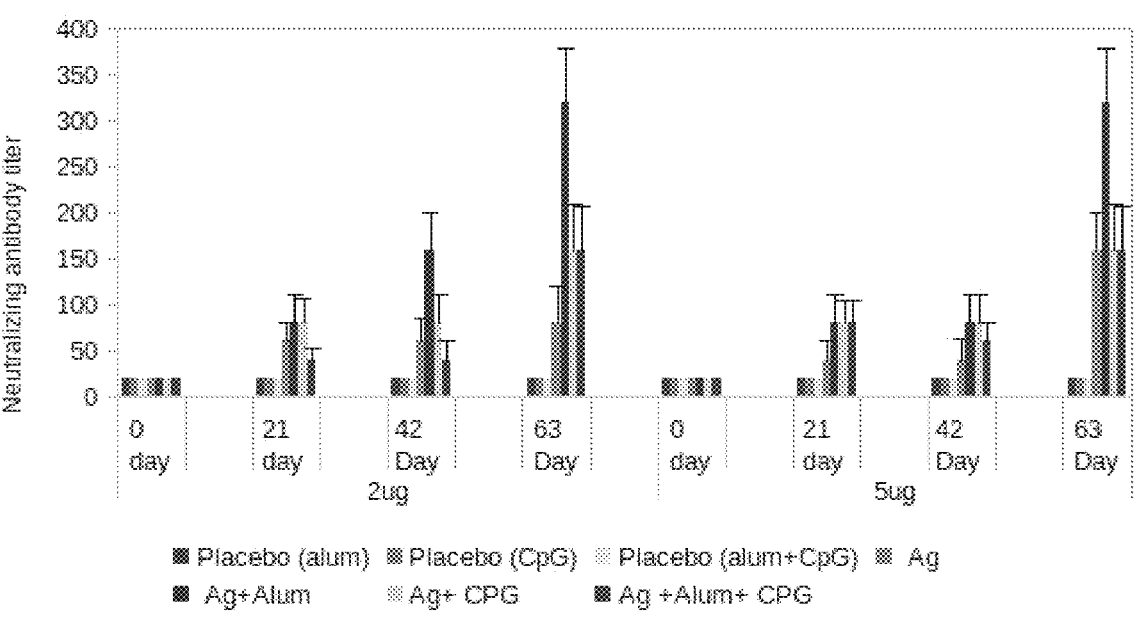

FIG. 20: Different formulation of IRV vaccination induces elevated levels of rotavirus-specific neutralizing activity in mice. Peripheral blood was collected before the mice received the first (day 0), second (day 21) and third (day 42) vaccination dose, and at the study endpoint (day 63). Levels of rotavirus-specific neutralizing activity in serum was determined by a microneutralization assay as described in the text. Data shows mean and error bar represent standard deviation. of n=5.

Figure 21:
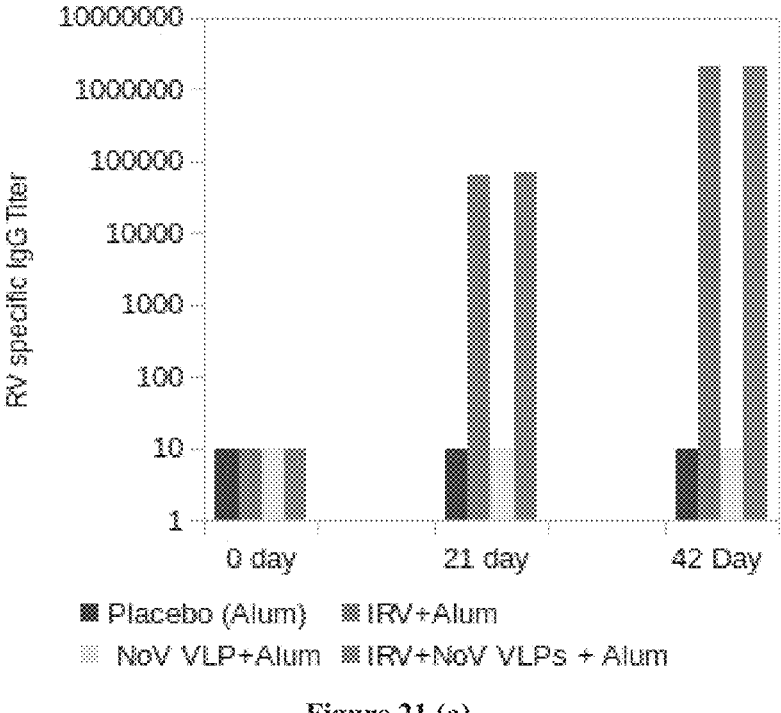
Figure 21:
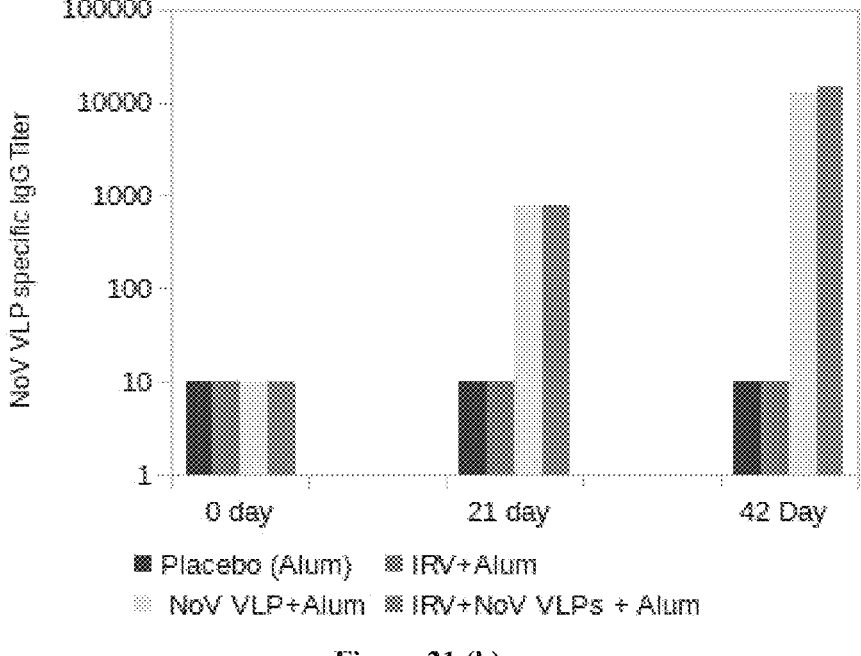

FIG. 21: IgG response to bivalent vaccine formulation described in Table 11. Sera from each group was pooled and evaluated for (a) RV specific IgG response [FIG. 21(a)] and (b) NoV-VLP specific IgG response [FIG. 21(b)]. Each serum specimen was tested at an initial dilution of 1:100. Pre-bleed serum specimens and placebo samples at all time points had no detectable antibody at this dilution, a value of 10 was used for representation.

Figure 22:
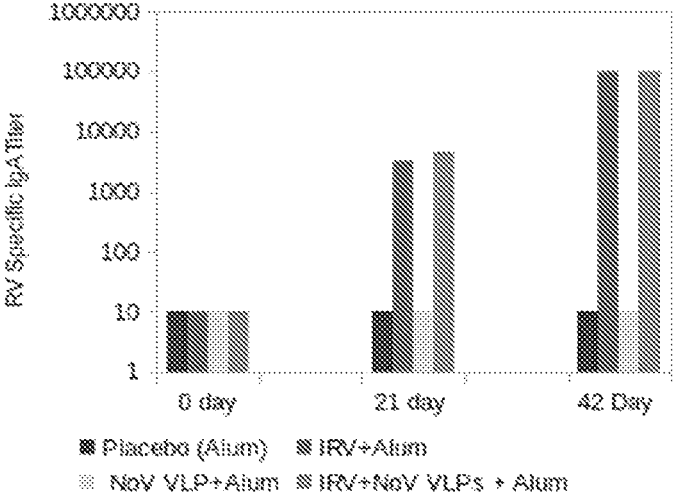
Figure 22:
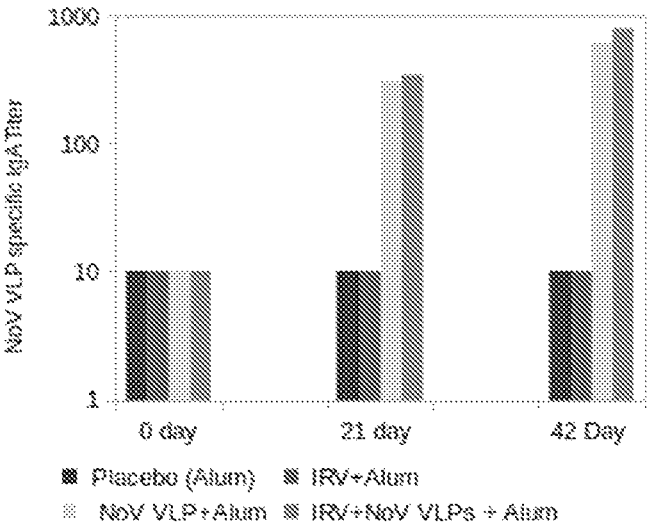

FIG. 22: IgA response to bivalent vaccine formulation described in Table 11. Sera from each group was pooled and evaluated for (a) RV specific IgA response [FIG. 22(a)] and (b) NoV-VLP specific IgA response [FIG. 22(b)]. Each serum specimen was tested at an initial dilution of 1:100. Pre-bleed serum specimens and placebo samples at all time points had no detectable antibody at this dilution and a value of 10 was used for representation.

FIG. 23:

(a) Neutralizing antibody titer against RV was determined by micro-neutralization assay described previously. Pooled sera from each group of mice was used. Sera was tested at an initial dilution of 1:20 and pre-bleed and placebo samples at all time points had no virus neutralization activity at this dilution and a value of 10 was used for representation.

(b) Surrogate neutralization assay for Norovirus. The blocking antibody titer for VLP-PGM binding was determined with pooled sera from each group of mice by method described in the text. Sera was tested at an initial dilution of 1:20 and pre-bleed and placebo samples at all timepoints had no VLP binding blocking activity at this dilution and a value of 10 was used for representation.

DETAILED DESCRIPTION OF THE INVENTION

The present invention provides methods of inactivation of rotavirus and vaccine compositions thereof. The invention discloses in particular, preparation and formulation of inactivated rotavirus antigen either as monovalent composition or in combination with other virus antigens including Norovirus VLPs.

Methods of rotavirus inactivation and vaccine composition containing inactivated rotavirus are provided in the present invention. The inactivation methods and vaccine formulation eliciting immune response is applicable to rotaviruses including human rotaviruses, simian rotaviruses, bovine, lapine, porcine, equine, canine, caprine, avian and murine rotaviruses. Further, the present invention is applicable to rotaviruses including rotaviruses of group A, B, C, D, E, F and G.

Rotavirus can be grown in vitro in cell culture. Rotavirus can be propagated in any permissive cells which allow the virus to grow well. For example, Vero, MA104, Caco-2, HT-29 cells etc. In a preferred embodiment, one such cell line used in the current invention is Vero cells which is validated for vaccine production.

For maintenance of the above-mentioned cell lines, specifically Vero cell line, stationary culture monolayers, perfusion system culture, shake flasks, roller tube/bottle culture, suspension culture, microcarrier culture, cell factories and cell stacks can be used. Various types of commercially available microcarriers and other animal cell culture devices can also be used.

In one embodiment of the current invention, rotavirus is purified to use as a vaccine candidate. Purification can be carried out either before or after inactivation of the virus. The virus can be purified by physical or chemical methods or a combination of both. Physical methods rely on the physical properties of the viruses and includes but not limited to zonal ultracentrifugation, density gradient centrifugation, ultrafiltration, diafiltration, concentration using semi-permeable membranes with suitable molecular cut-off sizes and size exclusion chromatography. The chemical methods include affinity chromatography, ion exchange chromatography, hydrophobic interaction chromatography, gel filtration chromatography etc.

The purified virus can be dialysed in suitable buffer and concentrated by diafiltration or by ultrafiltration membrane. Virus inactivation can be performed before or after purification.

Rotavirus can be inactivated by heat, chemical means or a combination of both heat and chemical agents. In one embodiment rotavirus was inactivated by heat by exposing it to a temperature in the range of about 40° C.-60° C. In further embodiments, rotavirus was inactivated by exposing to a temperature in the range of about 40° C.-50° C. The incubation time to inactivate rotavirus at a selected temperature is in the range of about 2 hours-10 days. In a preferred embodiment rotavirus was inactivated by exposing to a temperature of 49° C. for 4 days.

In another embodiment rotavirus was inactivated by chemical means. The chemical inactivating agents may include by not limited to formalin, beta-propiolactone, glutaraldehyde, hydrogen peroxide, N-acetylethyleneimine, binary ethyleneimine, tertiary ethyleneimine, ascorbic acid, caprylic acid, psolarens, detergents including non-ionic detergents etc. In one embodiment of the invention, the chemical inactivating agent is formalin. Formalin is used at any concentration ranging from 1:1000 to 1:4000 v/v of formalin:virus. Time required for complete virus inactivation was optimized in temperatures ranging from 4° C.-37° C. at a particular formalin concentration. In a preferred embodiment the virus was inactivated by 1:2000 v/v of formalin:virus at 25° C. or 37° C. for 8 days and 4 days respectively. While in another embodiment virus was inactivated by 1:4000 v/v of formalin:virus at 25° C. or 37° C. for 10 days and 6 days respectively. Formalin concentration, incubation time and temperature were optimized to obtain complete viral inactivation with minimal adverse effect on immunogenicity.

In another embodiment of the present invention, rotavirus was inactivated by hydrogen peroxide. The final concentration of hydrogen peroxide used ranges from 0.05% to 3%. Virus was incubated with aforementioned hydrogen peroxide concentration at 4° C. to 25° C. for a period of 4-48 hours. In a preferred embodiment the virus was inactivated by 3% hydrogen peroxide (final concentration) at 4° C. or 25° C. for 24 hours and 5 hours respectively. While in another embodiment virus was inactivated by 1% hydrogen peroxide (final concentration) at 4° C. or 25° C. for 48 hours and 24 hours respectively.

In a further embodiment rotavirus was inactivated by a combination of both heat and chemical agent. The objective was to reduce the concentration, time and temperature required for the virus inactivation by a single method. Reduction of the time and concentration of inactivating agent also maintained the antigenic structure of the virus better compared to single inactivation method. The chemical inactivating agent was selected from but not limited to formalin, beta-propiolactone, glutaraldehyde, hydrogen peroxide, N-acetylethyleneimine, binary ethyleneimine, tertiary ethyleneimine, ascorbic acid, caprylic acid, psolarens, detergents including non-ionic detergents etc. The temperature used in this inactivation method ranges from 40° C.-60° C. In one preferred embodiment the chemical inactivation agent is formalin, used at a concentration ranges from 1:5000 (formalin:virus, v/v) to 1:50000 (formalin:virus, v/v). In a specific embodiment of the invention rotavirus was inactivated by formalin concentration of 1:10000 (formalin: virus, v/v) at temperature ranges from 42° C.-55° C. for 4 hours to 4 days. In a more preferred embodiment rotavirus was inactivated by formalin concentration of 1:10000 (formalin:virus, v/v) at 49° C. or 55° C. for 24 hours and 4 hours respectively.

Rotaviruses inactivated by the aforementioned methods of the present invention retain a substantially intact rotavirus particle. The starting preparation of rotavirus particles may include either triple layer particle or double layer particle or both double-layer and triple-layer rotavirus particles. Rotaviruses inactivated by methods of the present invention substantially retain one or more intact viral proteins present in live rotavirus.

Purified rotavirus particles are filtered using a filter having a pore size in the range of about 0.2 to 0.8 micron. The inactivated virus particles are diluted in any pharmaceutically acceptable suitable buffer includes but not limited to phosphate buffer, citrate buffer, phosphate citrate buffer, tris (hydroxymethyl) aminomethane (Tris) containing buffer, borate buffer, glycine buffer, acetate buffer, succinate buffer, HEPES buffer, maleate buffer, PIPES buffer, MOPS buffer, MOPSO buffer or histidine buffer. The pH of the buffer ranges from pH 5-pH 9. The buffer may contain sodium chloride at a concentration of 50 to 200 mM and at least one salt of a divalent cation including, but not limited to, $CaCl_2$, $MgCl_2$ and $MgSO_4$ at a concentration 1 mM to 20 mM. The vaccine may also contain preservatives and stabilizers. The preservative may include but not limited to 2-phenoxy ethanol at a concentration of 2.5 to 5 mg per dose. The stabilizers include but not limited to reducing and non-reducing sugars, sugar alcohols such sorbitol and mannitol, glycerol, amino acids in the range of 0.01% to 10% for the liquid formulation. Optionally, the vaccine can also be lyophilized and reconstituted in a pharmaceutically acceptable buffer for administration intradermally/30 subcutaneously/intramuscularly/intravenously in human host.

In another embodiment of the present invention, an adjuvant is optionally included in the vaccine formulation. Adjuvants can reduce the amount of antigen required in the vaccine composition. Adjuvants are known in the art and include but not limited to Freund's adjuvant, aluminium hydroxide, aluminium phosphate, aluminium oxide, CpG, iron oxide, inulin of any polymorphic form, algammulin which is a combination of inulin and aluminum hydroxide, aluminium sulphate phosphate, calcium phosphate; liposomes, chitosan, saponin, complex carbohydrates, vegetable oils, bacterial lipopolysaccharides, peptidoglycans, monophosphoryl lipid (MPL), monophosphoryl lipid A (MPLA) and proteoglycans. In a preferred embodiment aluminium hydroxide and CpG was used for dose ranging studies.

In the present invention, rotavirus antigen used to elicit robust immune response, can be used at concentration range from 0.10 µg up to 100 µg per dose. In a preferred embodiment the concentration may fall anywhere between 0.10 µg up to 50 µg per dose. The vaccine can be administered with and without an adjuvant as both the inactivated vaccine and the adjuvanted formulations elicit good immune response. The vaccine can be administered as a single dose or in two or more doses to elicit effective immune response. A suitable schedule for administration of vaccine composition depends on age and health status of the subject, type of vaccine composition used, route of administration etc.

Induction of protective immunological response after vaccination can be determined by various methods including detection of anti-rotavirus antibodies, measurement of virus neutralizing antibody titer and/or by lymphocyte proliferation assay. Induction of immunological response can be detected in rotavirus disease condition in vaccinated subjects. Reduction of clinical signs and symptoms of rotavirus-mediated disease such as reduction of the amount of virus shed in feces, reduction of the number of days on which virus is shed in faeces, reduction in the number of days the subject has diarrhoea, reduction in mortality, reduction in morbidity, reduction in weight loss or weight gain.

The route of vaccine administration can be selected from, but not limited to intradermal, subcutaneous, intramuscular, intravenous, oral and intranasal routes. In a preferred embodiment of the invention, the preferred route is intramuscular (IM) route. The present invention also provides various vaccine formulations and methods to produce and formulate thereof e.g. a combination of inactivated rotavirus vaccine (IRV) and Norovirus vaccine (NoV-VLPs).

Norovirus antigens present in this invention include, but not limited to, antigenic capsid proteins or peptides either in the monomeric, multimeric or in virus like particle (VLP) form. VLPs" refer to fragment(s), or portion(s) or the whole capsid protein coding sequence of norovirus and comprising antigenic characteristic(s) similar to those of infectious norovirus particles. VLPs can be any structural proteins wherein the structural proteins are encoded by one or more nucleic acid sequences. VLPs may be spontaneously formed upon purification of recombinant structural proteins, i.e., self-assembling or intact VLPs, or aggregated VLPs. VLPs are morphologically and antigenically similar to authentic virions. VLPs may be produced in suitable host cells, e.g., mammalian, yeast, bacterial, and insect host cells. Norovirus antigens can be derived from any norovirus genotype of genogroup GI and GII. In a specific embodiment, norovirus antigen is GII.4 VLP. Norovirus antigen can be monovalent or bivalent or trivalent belonging to the same genogroup or different genogroup. Norovirus VLPs can be derived from either expression of only VP1 protein or by co-expression of VP1 and VP2 in a suitable host. The expression system can include but not limited to, yeast cells, bacterial cells, insect cells and mammalian cells. Suitable expression vectors for each expression system are well known to a person skilled in the art. The antigenic sequence of VP1 and VP2 can be synthesized representing a single isolate or a chimera representing different isolate from the same genotype.

In a specific embodiment, norovirus VP1 sequence from a single isolate or a chimera from different isolates of GII.4 was synthesized and cloned into a suitable vector for expression of the protein in yeast specifically in *Pichia pastoris*.

The VLPs can be purified by physical or chemical methods or a combination of both. The methods may include but not limited to zonal ultracentrifugation, density gradient centrifugation, ultrafiltration, diafiltration and concentration using semi-permeable membranes with suitable molecular cut-off sizes, different chromatographic methods, e.g. affinity chromatography, ion exchange chromatography, hydrophobic interaction chromatography, gel filtration chromatography etc. In a specific embodiment the VLPs were purified by a combination of density gradient ultracentrifugation, ion exchange chromatography and size exclusion chromatography. The purity of the VLPs may be evaluated by the presence of foreign proteins assayed by any appropriate method including, but not limited to gel electrophoresis and staining, western blot analysis, HPLC and/or ELISA assay. The integrity of the VLPs can be assessed by methods including but not limited to transmission electron microscopy (TEM), VLP binding to salivary antigens and/or porcine mucine etc. Purified VLPs can be diluted in any suitable buffer including but not limited to phosphate buffer, citrate buffer, phosphate citrate buffer, tris (hydroxymethyl) aminomethane (Tris) containing buffer, borate buffer, glycine buffer, acetate buffer, succinate buffer, HEPES buffer etc. With pH ranges from pH 5-9. In a specific embodiment the suitable buffer is 50 mM phosphate buffer pH-7.4±0.2. The vaccine may contain preservative(s) and stabilizer(s).

The present invention further provides a norovirus liquid vaccine formulation comprising of; i) purified norovirus VLPs; ii) 50 mM phosphate buffer, pH 7; which is stable for 6 months at 4° C.

The present invention provides methods to evaluate the immunogenicity of norovirus VLPs alone or immunogenicity and immune-interference of the VLPs with other antigens for example with inactivated rotavirus antigens. The immunogenicity of the VLP can be evaluated in Balb/C mice in a dose ranging from 0.1 μg to 40 μg with or without adjuvant. The adjuvant may include but not limited to aluminium (provided as aluminium hydroxide, dose range of 0.1 mg to 1.5 mg), inulin, a combination of aluminium hydroxide and inulin, MPL, a combination of aluminium hydroxide and MPL. Immunogenicity can be evaluated by methods include but not limited to VLP-Specific ELISA to determine the titer of immunoglobulin A (IgA), immunoglobulin G (IgG), IgG1, and IgG2a antibodies, neutralizing antibody titer evaluation by in vitro salivary PGM-VLPs binding blockade assay, in vitro Antigen-Specific Proliferation Assay, VLP-specific ELISPOT assay to evaluate VLP-specific antibody-secreting cell (ASC), determination of T-cell response and memory B-cell response etc. The vaccine can be used as single dose, two dose or more than two doses in a suitable schedule. The route of administration can be selected from, but not limited to intradermal, subcutaneous, intramuscular, intravenous, oral and intranasal routes. In a preferred embodiment of the invention, the route is intramuscular (IM) route.

In a combination vaccine, the antigen for both IRV and norovirus VLPs can be present at a concentration ranging from 0.2 μg to 50 μg in a pharmaceutically stable formulation with or without adjuvant. Immunogenicity of the combination vaccines can be evaluated in suitable hosts and immune response for each component can be analyzed independently. Immune response to IRV and norovirus VLPs can be assessed by methods already disclosed in the current invention.

Combination vaccine confers an economical advantage in terms of manufacturing, distribution and storage of the vaccines. A new vaccine can be easily introduced into the already crowded vaccination schedule in the form of combination vaccine, provided that immune response is elicited against each of the antigen in the formulation and no negative antigenic interference is observed. The vaccine antigens can either be administered from a single formulation or administered separately at the same time or in suitable time intervals so as to elicit an immune response to the cognate antigen.

EXAMPLES

Example 1: Rotavirus Culture in Vero Cells

Vero cells were grown in DMEM (Dulbecco's Modified Eagle Medium) or EMEM (Eagles Minimal Essential Medium) containing 5% fetal bovine serum (FBS) and incubated at 35° C.±1° C. until confluent monolayer is formed. Rotavirus was activated with trypsin at a concentration of 15 μg/ml and $CaCl_2$ at a concentration of 600 μg/ml for 1 hr at 35° C.±1° C. Confluent monolayer of vero cells were infected with activated rotavirus at a Multiplicity of Infection (MOI) of 0.04. Infected culture was harvested in batches after 3, 5 and 7 days post infection.

Example 2: Rotavirus Purification

Figure 1:
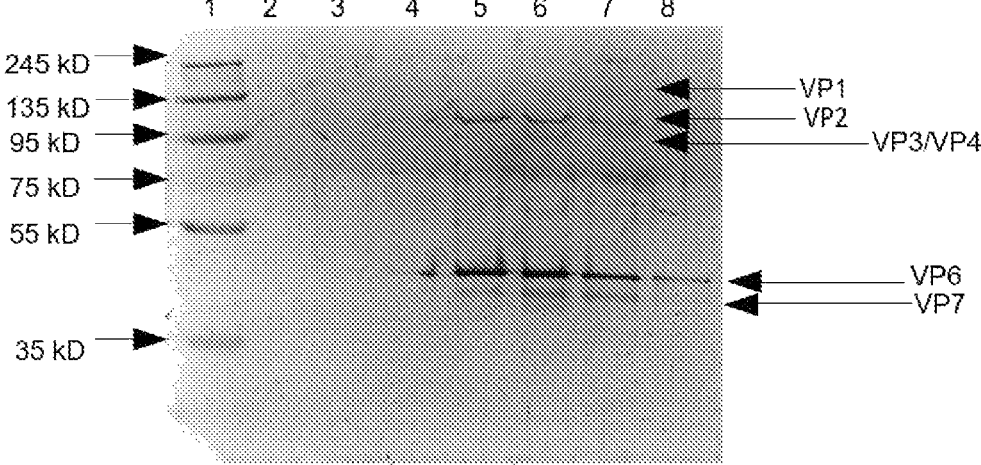
FIG. 1: Rotavirus was purified by sucrose cushion was run on 12% SDS-PAGE and silver stained. The structural proteins were detected. Lane 1, Molecular weight marker, Lane 2-8, 1 ml fractions collected from the bottom of the tube after ultracentrifugation. Fractions in lane 5-8 contain purified rotavirus particle.

The harvested virus was clarified by microfiltration using 0.45 μM filter. The clarified viral harvest was concentrated by diafiltration using either 100 kDa or 300 kDa cut off membranes. The clarified virus was purified by sucrose cushion method using ultracentrifugation at 100,000×g for 2 hours. The virus was collected from the interface of 40% and 70% sucrose. This fraction contains both double layer and triple layer rotavirus particle. The purity of the virus preparation was checked by silver staining of the virus sample in 12% SDS-PAGE gel as depicted in FIG. 1. The concentrated virus sample was dialyzed and inactivated by the methods described in subsequent sections. In an alternative method, the concentrated virus sample after diafiltration was inactivated first and then purified. The virus could also be purified by methods including but not limited to ion exchange chromatography, size exclusion chromatography, affinity chromatography, hydrophobic interaction chromatography and in all cases followed by diafiltration using 100 or 300 kDa cut off membranes.

Example 3: Stability of Rotavirus in Different Buffers

Figure 2:
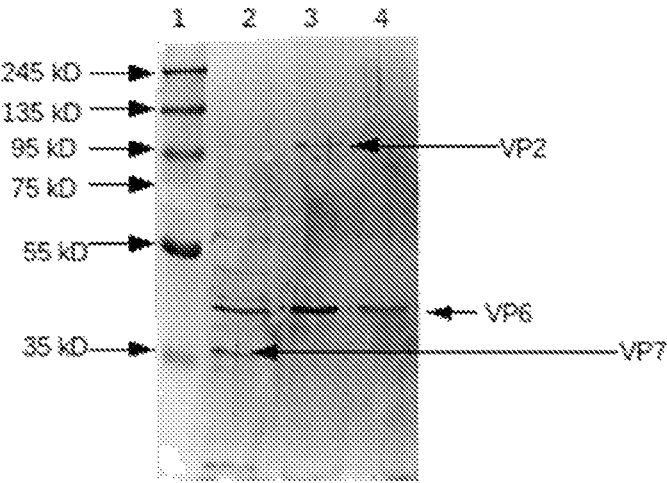
FIG. 2: Purified rotavirus was dialyzed in HBSS buffer and TNC buffer and run on 12% SDS-PAGE and silver stained. Lane 1: Molecular weight marker, Lane 2: Rotavirus bulk (before purification), Lane 3: purified rotavirus dialyzed against TNC buffer. Lane 4: purified rotavirus dialyzed against HBSS buffer.

Stability of rotavirus was evaluated in different buffers. After purification of live rotavirus by sucrose cushion method, purified virus was dialyzed in two different buffers, namely HMS buffer and TNC buffer (10 mM Iris, 140 mM NaCl, 10 mM $CaCl_2$). Stability of the virus in the above-mentioned buffers was evaluated by SDS-PAGE followed by silver staining to detect viral proteins. The result showed that the viral proteins are more stable in TNC buffer (FIG. 2).

Example 4: Rotavirus Inactivation by Heat

Figure 3:
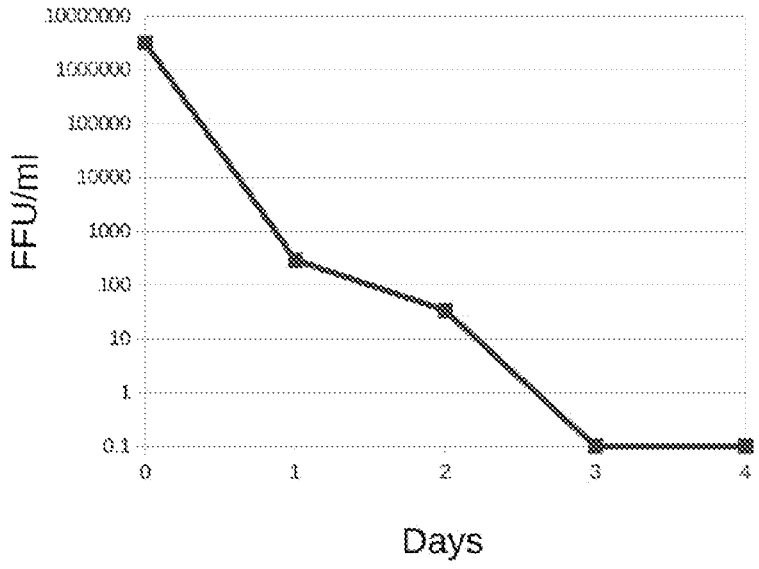
FIG. 3: Inactivation kinetics of rotavirus 116E at 49° C.

The virus in the cell culture supernatant obtained after clarification was inactivated by heat at temperatures ranging from 42° C.-60° C. for 30 mins to 10 days. Alternatively, the virus was first purified and then inactivated by heat at temperatures ranging from 42° C.-60° C. for 30 mins to 10 days in different buffers, and preferably at 49° C. for 4 days. The inactivation kinetics at different temperature has been demonstrated in Table 1 and inactivation kinetics specifically at 49° C. has been depicted in FIG. 3. The buffers include but not limited to phosphate buffer, citrate buffer, phosphate citrate buffer, tris (hydroxymethyl) aminomethane (Tris) containing buffer, borate buffer, glycine buffer, acetate buffer, succinate buffer, HEPES buffer, maleate

TABLE 1

| Heat inactivation of rotavirus 116E at different condition | | | | | | | | | |
|---|---|---|---|---|---|---|---|---|---|
| | Virus sampling time during inactivation kinetics | | | | | | | | |
| Temp | 1 day | 2 day | 3 day | 4 day | 5 day | 6 day | 7 day | 8 day | 9 day |
| 42° C. | ++ | ++ | ++ | ++ | ++ | ++ | ++ | -- | -- |
| 45° C. | ++ | ++ | ++ | ++ | ++ | ++ | -- | -- | -- |
| 47° C. | ++ | ++ | ++ | ++ | ++ | -- | -- | -- | -- |
| 49° C. | ++ | ++ | -- | -- | -- | -- | -- | -- | -- |

++ indicates presence of residual virus particle at particular point of sampling by immunoperoxidase assay
-- indicates absence of residual virus particle at particular point of sampling by immunoperoxidase assay

Example 5: Rotavirus Inactivation by Chemical Methods

Figure 4:
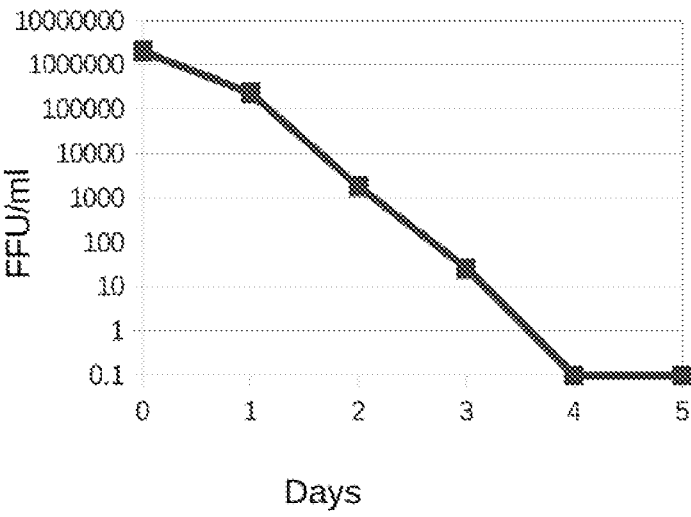
FIG. 4: Inactivation kinetics of rotavirus 116E by 1:4000 (formalin:virus, v/v) at 37° C.
Figure 5:
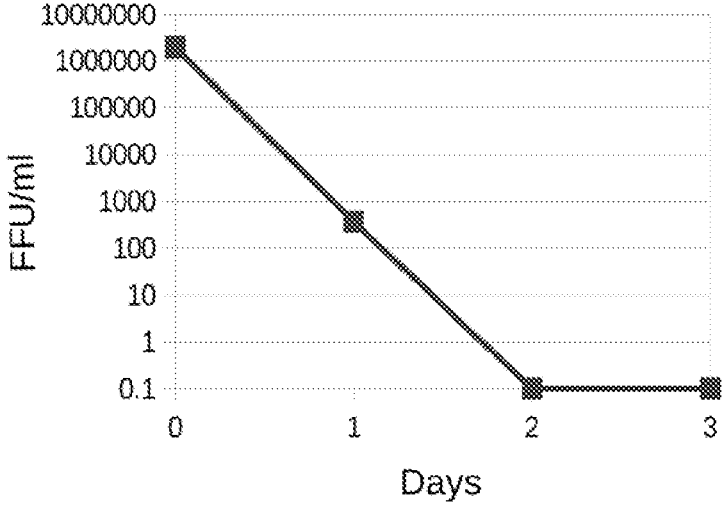
FIG. 5: Inactivation kinetics of rotavirus 116E by 1:2000 (formalin:virus, v/v) at 37° C.

Rotavirus sample was inactivated by various chemical methods for use as vaccine antigens. Formalin inactivation was tested at various concentrations ranging from 1:1000 (formalin:virus, v/v) to 1:4000 (formalin:virus, v/v) at temperature 25° C.-37° C. Preferably at 1:2000 (formalin:virus, v/v) and 1:4000 (formalin:virus, v/v) for 6 days and 4 days respectively, which is depicted in FIG. 4 and FIG. 5 respectively. The kinetics of virus inactivation was monitored at regular interval from few hours to up to 10 days, results of which have been provided in Table 2. Virus inactivation kinetics by formalin (two different concentration) at 37° C. have been shown in FIG. 4 and FIG. 5. After inactivation formalin was inactivated by sodium bisulfate ($NaHSO_3$) or sodium metabisulfite ($Na_2S_2O_5$).

TABLE 2

| Inactivation of rotavirus 116E by formalin at different condition | | | | | | | | | | | |
|---|---|---|---|---|---|---|---|---|---|---|---|
| Formalin | | Virus sampling time during inactivation kinetics | | | | | | | | | |
| concentration | Temp | 1 day | 2 day | 3 day | 4 day | 5 day | 6 day | 7 day | 8 day | 9 day | 10 day |
| 1:4000 | 25° C. | ++ | ++ | ++ | ++ | ++ | ++ | ++ | ++ | ++ | -- |
| | 37° C. | ++ | ++ | ++ | ++ | ++ | -- | -- | -- | -- | -- |
| 1:2000 | 25° C. | ++ | ++ | ++ | ++ | ++ | ++ | ++ | -- | -- | -- |
| | 37° C. | ++ | +- | -- | -- | -- | -- | -- | -- | -- | — |

++ indicates presence of residual virus particle at particular point of sampling by immunoperoxidase assay
-- indicates absence of residual virus particle at particular point of sampling by immunoperoxidase assay buffer, PIPES buffer, MOPS buffer, MOPSO buffer or histidine buffer. The pH of the buffer ranges from pH 5-pH 9, and more particularly at pH 7.4. The buffer may contain sodium chloride at a concentration of 50 to 200 mM and at least one salt of a divalent cation including, but not limited to, $CaCl_2$, $MgCl_2$ and $MgSO_4$ at a concentration 2 mM to 20 mM. In another embodiment the inactivation of rotavirus is carried out in the presence of a stabilizing agent selected from lactose, sucrose, trehalose, maltose, mannose, isomaltose, raffinose, stachyose, lactobiose, sorbitol, mannitol, lactobionic acid, dextran, L-glycine, L-histidine, L-glutamic acid and L-aspartic acid. Inactivated samples were taken at regular interval and residual infectivity of the virions was checked by methods described in subsequent section. Inactivation kinetics were derived in each case.

Figure 6:
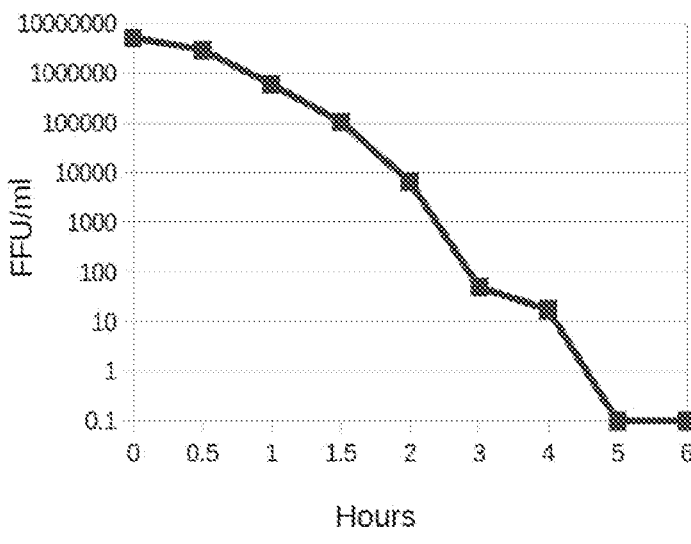
FIG. 6: Inactivation kinetics of rotavirus 116E by 3% hydrogen peroxide at 25° C.

Rotavirus inactivation was also carried out by hydrogen peroxide at a final concentration ranging from 0.05% to 3% at 4° C. to 25° C. for a period of 4-48 hours, preferably with 3% hydrogen peroxide for 6 hours. Inactivation kinetics has been provided in Table 3 and FIG. 6. To remove residual hydrogen peroxide, inactivated virus samples were treated with catalase at a final concentration of 12.5 U/ml-50 U/ml for 10 mins at room temperature. This procedure was performed twice on each sample to ensure complete removal of $H_2O_2$. The inactivated virus samples after exposure to different time and dose concentrations were titered for infectious virus particles if any by methods described in subsequent section.

TABLE 3

Inactivation of rotavirus 116E by hydrogen peroxide at different condition

| H₂O₂ concentration | Temp | Virus sampling time during inactivation kinetics | | | | | | | | | |
|---|---|---|---|---|---|---|---|---|---|---|---|
| | | 1 hr | 2 hr | 3 hr | 4 hr | 5 hr | 6 hr | 7 hr | 8 hr | 24 hr | 48 hr |
| 1% | 4° C. | ++ | ++ | ++ | ++ | ++ | ++ | ++ | ++ | ++ | -- |
| | 25° C. | ++ | ++ | ++ | ++ | ++ | ++ | ++ | ++ | -- | -- |
| 3% | 4° C. | ++ | ++ | ++ | ++ | ++ | ++ | ++ | ++ | ++ | -- |
| | 25° C. | ++ | ++ | ++ | +- | -- | -- | -- | -- | -- | -- |

++ indicates presence of residual virus particle at particular point of sampling by immunoperoxidase assay
-- indicates absence of residual virus particle at particular point of sampling by immunoperoxidase assay

Figure 7:
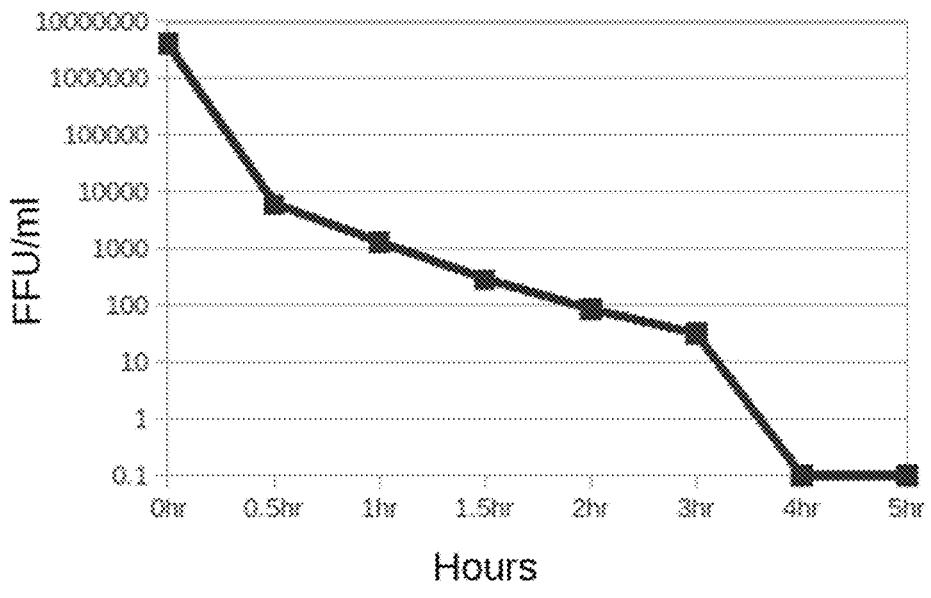
FIG. 7: Inactivation kinetics of rotavirus 116E by 1:10000 (formalin:virus, v/v) at 55° C.

Example 6: Rotavirus Inactivation by Combination of Heat and Chemical Methods Rotavirus was also inactivated with a combination of heat and formalin at temperature ranging from 40° C.-55° C. in presence of low concentration of formalin ranges from 1:5000 (formalin:virus, v/v) to 1:50000 (formalin:virus, v/v). The virus was inactivated in the aforementioned condition between 2-24 hr. Specifically at 49° C. and 55° C. for a period of 24 hrs and 4 hrs respectively. Inactivation kinetics are provided in Table 4 and inactivation kinetics specifically at 55° C. with a formalin concentration 1:10000 (formalin:virus, v/v) is provided in FIG. 7.

staining reagent. Live virus containing cells took pink to red stain. The stained cells were counted and viral titer was determined. If no stained cell is observed at a particular inactivation condition, MA104 cells in T25 flask was infected with the undiluted virus sample (trypsin activated) and incubated at 36±1° C. for 7 days. Infected cell cultures are then subjected to a second and third round of amplification in MA104 cells in the same manner for another 7 days for each round of replication. The culture supernatant was tested in immunoperoxide assay to visualize any life virus. The virus sample was considered inactivated if no virus infected cell is detected. The sensitivity of this method was

TABLE 4

Inactivation of rotavirus 116E by combination of heat and formalin at different condition.

| Formalin concentration | Temp | Virus sampling time during inactivation kinetics | | | | | | | | | | | |
|---|---|---|---|---|---|---|---|---|---|---|---|---|---|
| | | 1 hr | 2 hrs | 3 hrs | 4 hrs | 5 hrs | 6 hrs | 8 hrs | 1 day | 2 days | 3 days | 4 days | 5 days |
| 1:10000 | 42° C. | ++ | ++ | ++ | ++ | ++ | ++ | ++ | ++ | ++ | ++ | -- | -- |
| | 45° C. | ++ | ++ | ++ | ++ | ++ | ++ | ++ | ++ | ++ | ++ | -- | -- |
| | 49° C. | ++ | ++ | ++ | ++ | ++ | ++ | ++ | -- | -- | -- | -- | -- |
| | 55° C. | ++ | ++ | ++ | -- | -- | -- | -- | -- | -- | -- | -- | -- |

++ indicates presence of residual virus particle at particular point of sampling by immunoperoxidase assay.
-- indicates absence of residual virus particle at particular point of sampling by immunoperoxidase assay.

Example 7: Determination of Complete Viral Inactivation

Complete viral inactivation and live viral count at each time point of inactivation was determined by immunoperoxidase assay. 1×10⁵ MA104 cells were seeded in 24 well plate 48 hrs prior the assay. Both control and inactivated virus was incubated with trypsin at a concentration of 15 μg/ml at 36±1° C. for 1 hr. Confluent monolayer of MA104 cells in 24 well plate was washed two times with serum free DMEM. 100 μl of serum free DMEM was added in each well. After activation, both control and test virus samples were serially diluted 10-fold in dilution medium (serum free DMEM+2 μg/ml trypsin) till 10⁻⁶ dilution. 100 μl of diluted samples were added in each well in duplicate/triplicate. For test samples, 100 μl of undiluted virus was also added to the cells. The virus was allowed to adsorb by the cells for 1 hr at 36±1° C. After adsorption, 500 μl of dilution media was added to each well and the plates were incubated at 36±1° C. for 12-16 hr. After incubation, cells were fixed with 10% formalin, permeabilized with 1% triton X100 and incubated with rabbit anti-rotavirus hyperimmune serum (1:5000) for 1 hr at 36±1° C. After washing two times with PBS the cells were incubated with HRP conjugated goat anti-rabbit IgG for 1 hr at 36±1° C. Then the cells were incubated with AEC established with control bulk virus at different dilution and it is found to be 0.1 FFU/ml. The data is shown in Table 5.

TABLE 5

Determination of rotavirus detection limit after passage in cell culture

| Virus titer | Virus detection after different passage | | |
|---|---|---|---|
| | 1ˢᵗ passage | 2ⁿᵈ passage | 3ʳᵈ passage |
| 10 FFU/ml | ++ | ++ | ++ |
| 1 FFU/ml | -- | ++ | ++ |
| 0.1 FFU/ml | -- | +/- | + |

++ indicates presence virus particle at particular point of sampling by immunoperoxidase assay.
-- indicates absence of virus particle at particular point of sampling by immunoperoxidase assay.
+/- indicates variable result (+ indicates present, - indicates absence) in detection of virus particle at particular point of sampling by immunoperoxidase assay

Example 8: Analysis of Inactivated Rotavirus

Figure 8:
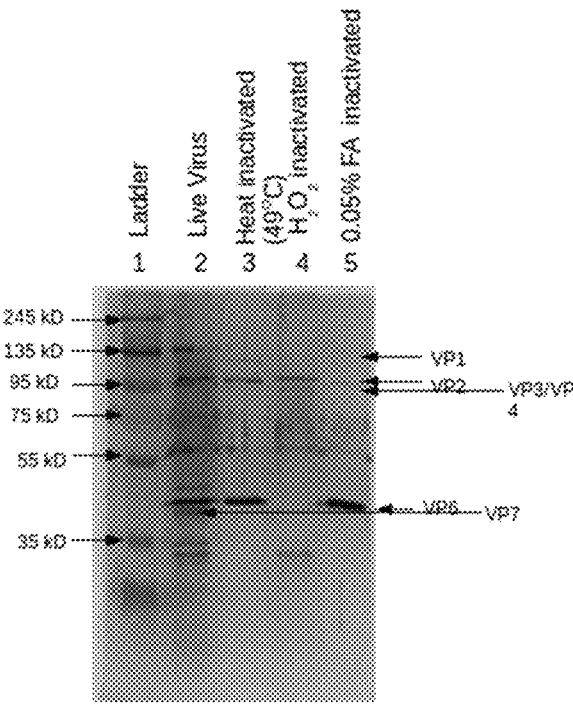
FIG. 8: Rotavirus was inactivated by different methods and purified by sucrose cushion. Live virus was also purified and was run on 12% SDS-PAGE along with the inactivated virus. The structural proteins were detected and compared between live and inactivated virus both by (a) silver staining [FIG. 8(*a*)] and (b) western blot with rabbit anti rotavirus polyclonal antibody [FIG. 8(*b*)]. Lane 1, Molecular weight marker, Lane 2: purified live virus, Lane 3: RV inactivated by heat (49° C., 4 hr) and purified, Lane 4: RV inactivated by 1% $H_2O_2$ and purified, Lane 5: RV inactivated by 0.05% formaldehyde and purified.
Figure 8:
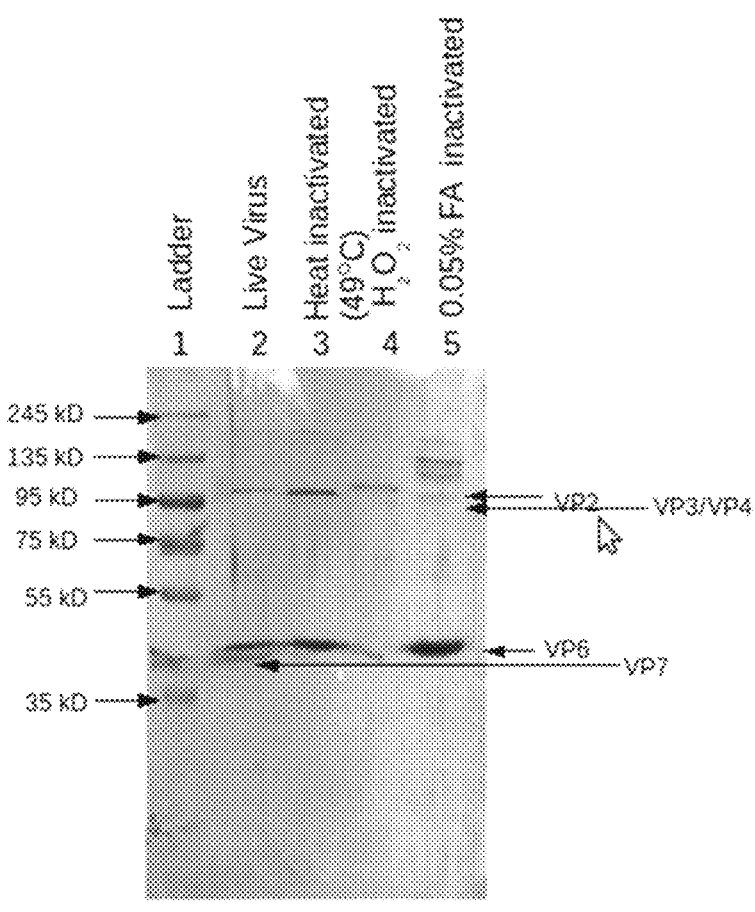

The purity and protein composition of rotavirus particles inactivated by different inactivation method of the present invention are determined by SDS-polyacrylamide gel electrophoresis followed by silver staining (FIG. 8*a*) or western blot analysis using rotavirus-specific rabbit hyperimmune serum (FIG. 8*b*). This analysis showed that inactivated virus particles contained all major structural viral proteins—VP1, VP2, VP4, VP6, and VP7, and are antigenic, as demonstrated by their detection in western blot analysis using rabbit hyperimmune serum. The protein concentration of purified particles was measured by the Pierce@ BCA Protein Assay (Thermo Scientific, USA) using bovine serum albumin as standards. After purification, rotavirus particles were filtered using a filter having a pore size in the range of about 0.2 to 0.8 micron.

Example 10: Stability of Norovirus VLPs

Stability of norovirus VLPs was monitored at 4° C. Purified VLPs were filtered using a filter having a pore size In one embodiment, an example pseudo-code segment for the schema of a generation request may take a form similar to the following: in the range of about 0.2 to 0.8 micron and stored 4° C. At regular intervals sample was taken and protein concentration was quantified by using a Pierce@ BCA Protein Assay. VLPs were found to be stable for 6 months at 4° C. (Table 6).

TABLE 6

| Norovirus VLP stability at 4° C. | | | | | | | |
|---|---|---|---|---|---|---|---|
| | 0 day | 1 month | 2 months | 3 months | 4 months | 5 months | 6 months |
| VLP Concentration | 0.5 mg/ml | 0.48 mg/ml | 0.43 mg/ml | 0.45 mg/ml | 0.44 mg/ml | 0.42 mg/ml | 0.42 mg/ml |

Example 9: Norovirus Vaccine Antigen Production

Figure 9:
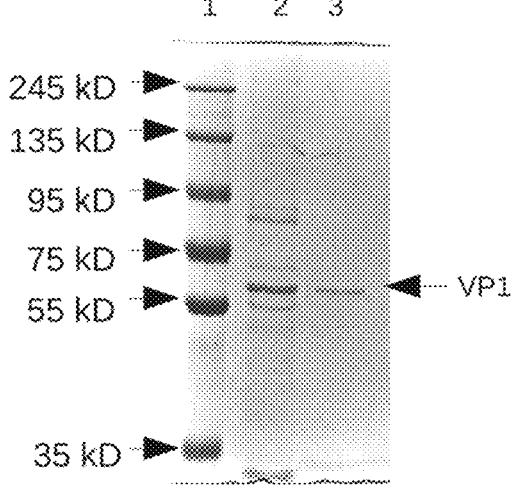
FIG. 9: Detection of purified VP1 (MW 59 kDa) protein in 12% SDS-PAGE by Coomassie staining. Lane 1: Molecular weight marker, Lane 2: sample after ultracentrifugation, Lane 3: purified VLPs.

Norovirus antigens present in this invention include, but not limited to, antigenic capsid proteins or peptides either in the monomeric, multimeric or in VLP form. Norovirus antigens can be derived from any norovirus genotype of genogroup GI and GII. In a specific embodiment, norovirus antigen is GII.4 VLP. Norovirus antigen can be monovalent or bivalent or trivalent belonging to the same genogroup or different genogroup. Norovirus VLPs can be derived from either expression of only VP1 protein or by co-expression of VP1 and VP2 in a suitable host. The expression system can include but not limited to yeast cells, bacterial cells, insect cells and mammalian cells. The antigenic sequence of VP1 and VP2 can be synthesized representing a single isolate or a chimera representing different isolate from the same genotype. Norovirus VP1 sequence from a single isolate (Seq 1) or a chimera from different isolates of GII.4 was synthesized (Seq 2) and cloned into a suitable vector (pPICZαA) for expression of the protein in yeast. The vector contained a secretion signal at N-terminus for directing secretion of expressed protein outside the cells. Stable transformants were produced in both Mut$^+$ and Mut$^S$ strain of *Pichia pastoris*. VP1 expression and secretion in medium was standardized. For VLP purification, culture supernatant was clarified by centrifugation at 13,000 rpm for 15 mins at 4° C. The VLPs were then concentrated by 40% sucrose cushion using P28S rotor in Hitachi HIMAC ultracentrifuge by centrifugation at 100,000×g for 2 hours. The precipitated VLPs were resuspended in suitable buffer such as 50 mM phosphate buffer, pH 7, and further purified by ion exchange chromatography. The purity of the protein was verified by 12% SDS-PAGE and shown in FIG. 9. VLPs can also be purified by any one or more combination of methods ranging from size exclusion chromatography, affinity chromatography, hydroxyapatite chromatography and hydrophobic interaction chromatography. The VLPs were finally concentrated and buffer exchanged by ultrafiltration using 10 kDa to 100 kDa cut off membrane. VLPs were stored at 4° C. and total protein concentration was quantified by using a Pierce@ BCA Protein Assay (Thermo Scientific, USA).

Example 11: Norovirus VLP Vaccine Formulation and Potency Testing in Animals The immunogenicity of the VLP was evaluated in Balb/C mice in a dose ranging from 0.1 to 40 µg with or without adjuvant. The adjuvant includes but not limited to aluminium (provided as aluminium hydroxide, dose range of 0.1 mg to 1.5 mg), inulin, a combination of aluminium hydroxide and inulin, MPL, a combination of aluminium hydroxide and MPL. The vaccine formulations can be prepared with or without stabilizers. Stabilizers may be selected from a range of stabilizers acceptable for the use in vaccine for human use. In another embodiment, norovirus VLPs are co formulated with rotavirus antigen. Immunogenicity of the combination vaccines against each antigen was also evaluated in animal model.

Vaccine formulation tested are summarized in Table 7.

TABLE 7

| Groups of mice for potency testing of different Norovirus VLP vaccine formulation | |
|---|---|
| Group | Vaccine formulation |
| Placebo (Alum) | 500 µg aluminium hydroxide/dose |
| Placebo (MPLA) | 5 µg MPLA/dose |
| Placebo (Alum + MPLA) | 500 µg aluminium hydroxide + 5 µg MPLA/dose |
| 2 µg Antigen | 2 µg NoV VLPs/dose |
| 2 µg Antigen + Alum | 2 µg NoV VLPs + 500 µg aluminium hydroxide/dose |
| 2 µg Antigen + MPLA | 2 µg NoV VLPs + 5 µg MPLA/dose |
| 2 µg Antigen + Alum + MPLA | 2 µg Antigen + + 500 µg aluminium hydroxide + 5 µg MPLA/dose |
| 10 µg Antigen | 10 µg NoV VLPs/dose |
| 10 µg Antigen + Alum | 10 µg NoV VLPs + 500 µg aluminium hydroxide/dose |
| 10 µg Antigen + MPLA | 10 µg NoV VLPs + 5 µg MPLA/dose |
| 10 µg Antigen + Alum + MPLA | 10 µg Antigen + + 500 µg aluminium hydroxide + 5 µg MPLA/dose |

Each group had 5-6 mice and vaccine formulation comprising 100 µl/dose was administered intramuscularly.

Figure 10:
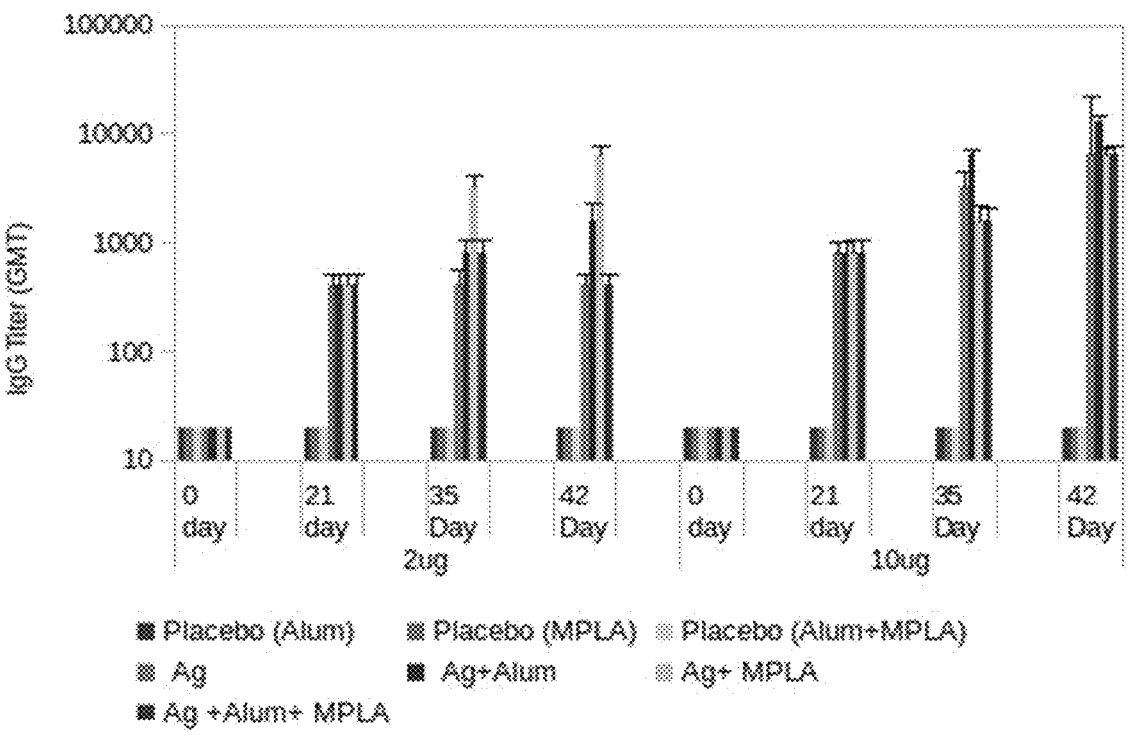
FIG. 10: IgG response to norovirus VLPs at different time point after vaccination was tested by ELISA described in the text. Mice were vaccinated I.M. twice with 2 μg or 10 μg of antigen either alone or with different combination of adjuvants (details are mentioned in Table 7). Each serum specimen was tested at an initial dilution of 1:100. Pre-bleed serum specimens and placebo samples at all timepoints had no detectable antibody at this dilution, a value of 20 was used for determining geometric mean titers and illustration. Antibody titers are expressed as the geometric means for each group (n=5 or 6). Error bars represent one standard deviation.
Figure 11:
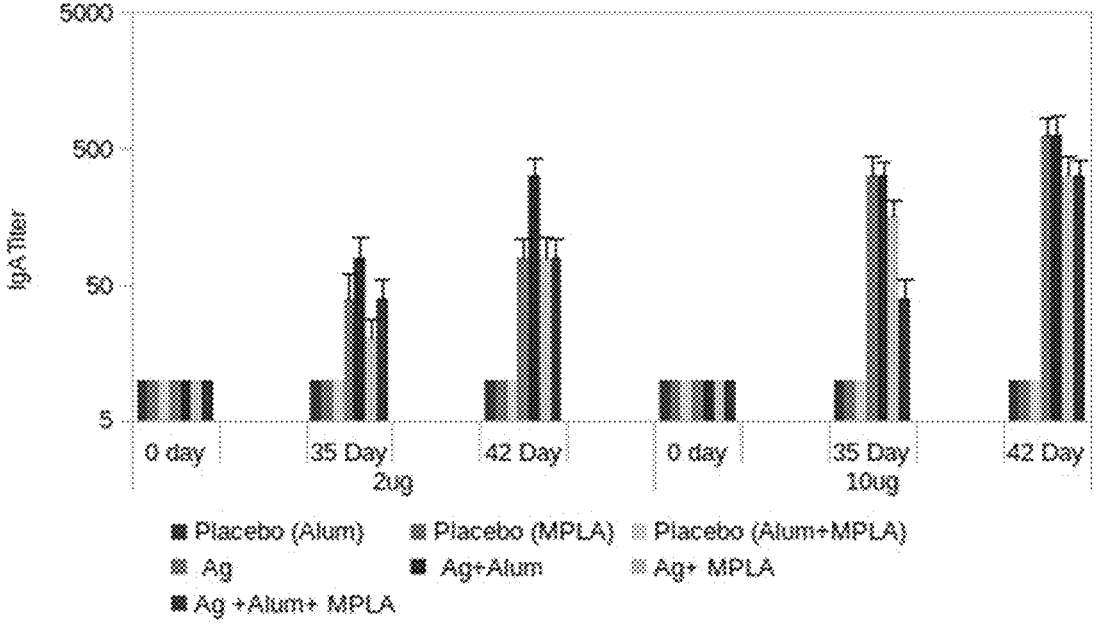
FIG. 11: IgA response to norovirus VLPs at different time point after vaccination. Mice were vaccinated I.M. twice with 2 μg or 10 μg of antigen either alone or with different combination of adjuvants. Each serum specimen was tested at an initial dilution of 1:20. Pre-bleed serum specimens and placebo samples at all timepoints had no detectable antibody at this dilution, a value of 10 was used for determining geometric mean titers and illustration. Antibody titers are expressed as the geometric means for each group (n=5 or 6). Error bars represent one standard deviation.
Figure 12:
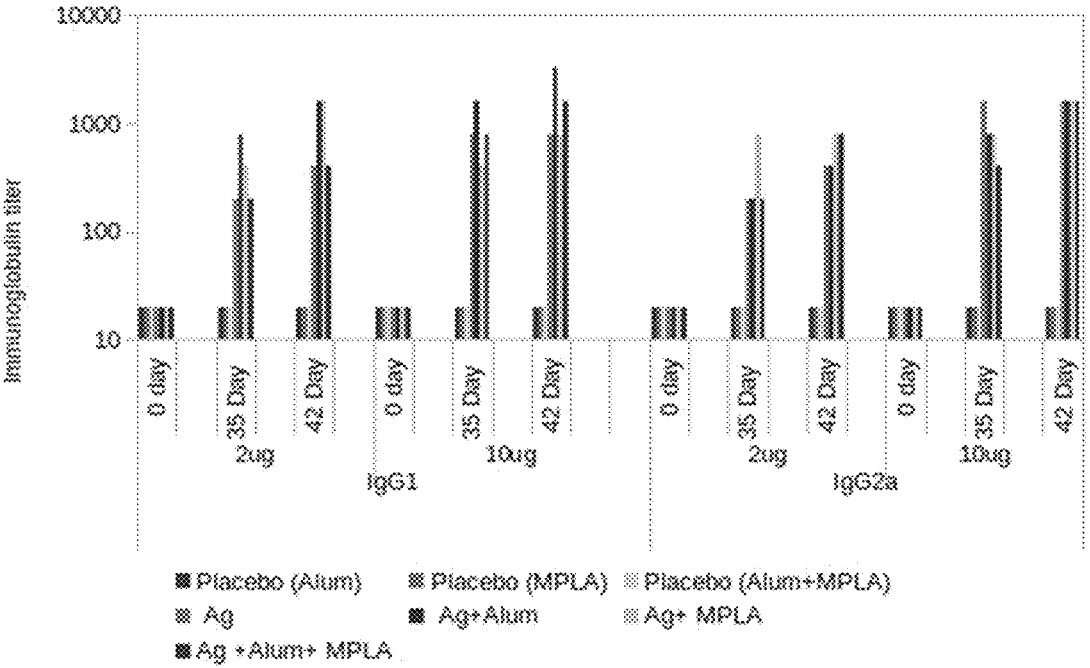
FIG. 12.
Figure 12:
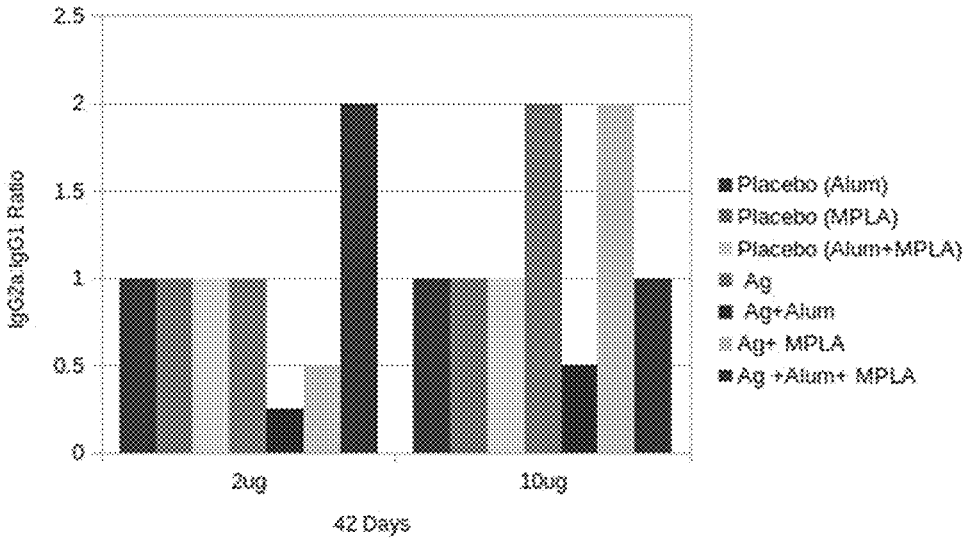

Mice were immunized two times, at $0^{th}$ and $21^{st}$ day. Blood was collected at weeks 0 (pre-bleed, non-immune sera), 2, 3, 4 and 5. The mice were euthanized at week 6 and final bleed was taken. Serum was separated and analyzed by ELISA. 96 well plates (Nunc Immuno Maxisorp) were coated with VLPs (100 ng per well) in carbonate-bicarbonate buffer (pH:9.5) at 4° C. for overnight. The wells were blocked with 5% (w/v) skimmed milk in phosphate buffered saline (PBS, pH:7.4) at room temperature for 1 hr, washed with PBS-0.05% Tween$^{-20}$. Serum samples of individual mice were serially diluted two-fold from 1:100 diluted in 1% skimmed milk in PBS and incubated at 37° C. for 1 hr. The bound IgG was detected by incubation with horse radish peroxidase (HRP) conjugated goat anti-mouse IgG (Sigma) diluted (1:2500) in 1% skimmed milk in PBS at 37° C. for 1 hr followed by substrate (Tetramethyl benzidine/H2O2, DeNovo Biolabs) addition. The reaction was stopped with 1 N HCl and absorbance (OD) at 450 nm was measured with an EIA reader. Each serum specimen was tested on VLP coated and buffer coated (negative control) wells and considered to be positive when absorbance (450 nm) of the VLP-coated well was 2 times or more than that of the buffer coated well (FIG. 10). IgA, IgG1 and IgG2a titer were also evaluated similarly with horse radish peroxidase (HRP) conjugated goat anti-mouse IgA (1:2000) (FIG. 11) goat anti-mouse IgG1 (1:2000) (FIG. 12a) and goat anti-mouse IgG2a (1:2000) (FIG. 12a) respectively. The ratio of IgG 2a:IgG1 was calculated from the titer and represented in FIG. 12b. The results showed that NoV VLPs at both the concentration tested were immunogenic and presence of adjuvant increased the immune response. Immune response in presence of aluminum hydroxide was Th2 biased (IgG 2a: IgG1<1) whereas immune response in presence of MPLA was Th1 biased (IgG 2a: IgG1>1).

One of the features of norovirus and therefore the VLPs derived from the capsid protein is that they can bind to the HBGA antigen in cell surface as well as in secretion from the secretor positive individual. Pig Gastric Mucin Type III (PGM) (Sigma Chemicals) has been validated as a substrate for NoV VLP [Costantini V, et al. (2012)]. PGM contains relatively high levels of H and A antigen and more moderate levels of Lewis Y antigen. Neutralizing antibody in serum control. The VLP mixture was then added to the carbohydrate ligand-coated plates for 1 hour. Bound VLP was detected by incubation with anti norovirus capsid protein VP1 specific primary ab (abcam, Ab92976) (1:2000) followed by incubation with HRP conjugated goat anti rabbit secondary antibody (1:2500) and color developed with TMB substrate solution (DeNovo Biolabs) and the reaction was stopped with 1N HCl and absorbance (OD) at 450 nm was measured with an EIA reader. The percent control binding was defined as the binding level in the presence of serum pretreatment compared to the binding level in the absence of serum pretreatment multiplied by 100. Neutralization titer or blocking titer 50 was determined based on the serum dilution at which the percent of binding was <=50%. All incubations were done at room temperature. Each step was followed by washing with PBS-0.05% Tween 20 and all reagents were diluted in 5% dry milk in PBS-0.05% Tween-20. FIG. 13 demonstrated neutralizing antibody titer of different vaccine formulation. All formulation induced neutralizing antibody, but presence of adjuvant, particularly aluminum hydroxide induced maximum response.

Example 12: Vaccine Formulation and Potency Testing of Rotavirus Antigen Inactivated by Different Methods The rotavirus particles were optionally lyophilized after inactivation for later resuspension in a pharmaceutically acceptable carrier. In one embodiment, vaccine compositions of the present invention which include both substantially intact triple-layer and double-layer rotavirus particle structure. The vaccine antigens inactivated by aforementioned methods were tested in Balb/c mice in dose ranging from 2 μg to 20 μg without adjuvant. Mice in a group of five were immunized with inactivated rotavirus antigen at two different concentration. Appropriate controls were taken. The detail description of vaccine formulation are summarized in Table 8.

TABLE 8

| Vaccine formulation and potency testing of rotavirus antigen inactivated by different methods | |
| --- | --- |
| Group | Vaccine formulation |
| Placebo | Only buffer |
| 2 μg Heat 60 deg | 2 μg of purified RV antigen inactivated by heat at 60° C. for 2 hrs/dose |
| 2 μg Heat 49 deg | 2 μg of purified RV antigen inactivated by heat at 49° C. for 4 days/dose |
| 2 μg 49 deg + FA | 2 μg of purified RV antigen inactivated by combination of heat at 49° C. and formalin (1:10000, formalin:virus, v/v) for 24 hrs/dose |
| 2 μg 55 deg + FA | 2 μg of purified RV antigen inactivated by combination of heat at 55° C. and formalin (1:10000, formalin:virus, v/v) for 4 hrs/dose |
| 5 μg Heat 60 deg | 5 μg of purified RV antigen inactivated by heat at 60° C. for 2 hrs/dose |
| 5 μg Heat 49 deg | 5 μg of purified RV antigen inactivated by heat at 49° C. for 4 days/dose |
| 5 μg 49 deg + FA | 5 μg of purified RV antigen inactivated by combination of heat at 49° C. and formalin (1:10000, formalin:virus, v/v) for 24 hrs/dose |
| 5 μg 55 deg + FA | 5 μg of purified RV antigen inactivated by combination of heat at 55° C. and formalin (1:10000, formalin:virus, v/v) for 4 hrs/dose | samples was evaluated by in vitro Mucin-VLPs binding blockade assay as described previously [Costantini V, et al. (2012)]. For blockade assays, PGM was dissolved in PBS at 5 mg/ml and coated onto EIA plates at 10 μg/ml in PBS for 4 hours and blocked over night at 4° C. in 5% dry milk in PBS-0.05% Tween-20. Pooled serum samples from each group of mice were serially diluted two-fold from 1:20 and incubated with VLPs (0.5 m g/ml) for 1 hour at room temperature. VLPs incubated with dilution buffer served as Mice were injected intramuscularly (IM) with a final volume of 100 μl for three times at 3 weeks interval. Blood was collected one day before each immunization and final bleed was taken on day 63. Serum was separated and immunogenicity was assayed by measuring immunoglobulin titer of both IgG and IgA. 96 well plates were coated with diluted rabbit hyperimmune serum raised against 116E rotavirus for overnight at 4° C. The wells were blocked with 5% (w/v) skimmed milk in phosphate buffered saline (PBS, pH:7.4) at room temperature for 1 hr, washed with PBS-0.05% Tween-20. The wells are then incubated with either 116E infected or mock infected supernatant of MA104 cells for 1 hr at 37° C. Serum samples of individual mice were serially diluted two-fold from 1:100 diluted in 1% skimmed milk in PBS and incubated at 37° C. for 1 hr. The bound IgG was detected by incubation with horse radish peroxidase (HRP) conjugated goat anti-mouse IgG (Sigma) diluted (1:2500) in 1% skimmed milk in PBS at 37° C. for 1 hr followed by substrate (Tetramethyl benzidine/$H_2O_2$, DeNovo Biolabs) addition. Each serum specimen was tested on virus containing as well as only cell supernatant containing well (negative control). The reaction was stopped with 1 N HCl and absorbance (OD) at 450 nm was measured with an EIA reader. Antibody titer in a serum was defined as the reciprocal of the highest dilution with a net OD value [(OD with RV minus OD with MA104 supernatant)-OD with 5% blotto] of greater than 0.1 (FIG. 14). IgA titer was also evaluated similarly with horse radish peroxidase (HRP) conjugated goat anti-mouse IgA (1:2000) (FIG. 15). Antibody titer in mice injected with inactivated and purified antigen of rotavirus 116E are compared with control mice as well as between mice injected with the antigen inactivated by different methods. Antibody titer in control mice was less than 100 and FIG. 14 and FIG. 15 demonstrated the IgG and IgA titer in different group of mice at different antigen concentration as well as at different time point. All rotavirus antigen prepared by different inactivation methods were found to be immunogenic.

Rotavirus-specific neutralizing activity was measured in a microneutralization assay with rotavirus strain 116E. In brief, mouse sera from days 0, 21, 42, and 63 were diluted two-fold in duplicates in 96-well plates and incubated with trypsin-activated 2000 FFU of 116E per well for 1 hour at 37° C. Activated rotavirus or similarly treated serum-free DMEM medium was incubated in the absence of sera and served as positive and negative controls, respectively. 3×105 MA104 cells in DMEM with 10 µg/ml trypsin (Invitrogen, Carlsbad, CA) and were added to each well and incubated at 37° C. for overnight in a humidified incubator. The plates were fixed with formalin and incubated with rabbit hyper-immune serum raised against 116E. RV antigen was detected with HRP-labeled goat anti-rabbit antibody and color was developed with TMB. Neutralizing antibody titer was defined as the reciprocal of the highest dilution that gave a greater than 60% reduction in the absorbance value when compared to virus-only controls. FIG. 16 represented the neutralizing antibody titer evoked by different rotavirus antigen.

Example 13: Vaccine Formulation and Potency Testing of Rotavirus Antigen with and without Adjuvants The best method of inactivation was selected based on the immune response obtained by antigen inactivated by different methods. Rotavirus 116E inactivated by heat at 49° C. for four days was found to be most immunogenic in terms of IgG, IgA response and serum neutralizing antibody (FIGS. 14, 15 and 16). Next, the rotavirus antigen inactivated by heat at 49° C. for four days was formulated with different adjuvant and immunogenicity was evaluated to select the best adjuvant. The adjuvant includes but not limited to aluminium (provided as aluminium hydroxide, dose range of 0.1 mg to 1.5 mg), CpG, a combination of aluminium hydroxide and CpG, inulin, MPL, a combination of aluminium hydroxide and MPL. In another embodiment the vaccine antigen also contained stabilizers.

Mice in a group of 5 were immunized parenterally with three doses at three weeks interval. Two different concentration of the antigen with different combination of adjuvant were tested. The formulations are summarized in Table 9.

TABLE 9

| Groups of mice for potency testing of different IRV vaccine formulation | |
|---|---|
| Group | Vaccine formulation |
| Placebo (Alum) | 500 µg aluminium hydroxide in TNC buffer/dose |
| Placebo (CpG) | 10 µg CpG in TNC buffer/dose |
| Placebo (Alum + CpG) | 50 µg aluminium hydroxide + 10 µg CpG in TNC buffer/dose |
| 2 µg Antigen | 2 µg Antigen in TNC buffer/dose |
| 2 µg Antigen + Alum | 2 µg Antigen + 500 µg aluminium hydroxide in TNC buffer/dose |
| 2 µg Antigen + CpG | 2 µg Antigen + 10 µg CpG in TNC buffer/dose |
| 2 µg Antigen + Alum + CpG | 2 µg Antigen + 50 µg aluminium hydroxide + 10 µg CpG in TNC buffer/dose |
| 5 µg Antigen | 5 µg Antigen in TNC buffer/dose |
| 5 µg Antigen + Alum | 5 µg Antigen + 500 µg aluminium hydroxide in TNC buffer/dose |
| 5 µg Antigen + CpG | 5 µg Antigen + 10 µg CpG in TNC buffer/dose |
| 5 µg Antigen + Alum + CpG | 5 µg Antigen + 50 µg aluminium hydroxide + 10 µg CpG in TNC buffer/dose |

Each group had 5-6 mice and vaccine formulation comprising 100 µl/dose was administered intramuscularly.

Blood was collected one day before each immunization and final bleed was taken on day 63. Serum was separated and rotavirus specific serum IgG, IgG1, IgG2a and IgA were measured by immunoassay described before. For detection of IgG1 and IgG2a, HRP conjugated anti mouse IgG1 (1:2000) and IgG2a (1:2000) was used. FIG. 17 and FIG. 18 demonstrated IgG and IgA response in different group of mice received different vaccine formulation. FIG. 19(a) depicted immune response in different vaccine group in terms of IgG subclasses (IgG1 and IgG2a). The ratio of IgG2a:IgG1 indicated the Th cell response with different vaccine formulation FIG. 19(b). A ratio of 1 indicates a balanced Th1 and Th2 response whereas a ratio of >1 represents Th1 biased immune response and a ratio of <1 represents Th2 biased immune response. All vaccine formulation tested induced a Th1 biased immune response but in presence of CpG the biasness was higher [FIG. 19 (b)].

Serum neutralizing antibody was also measured by a microneutralization assay described before.

Presence of adjuvant increased the degree of immune response (FIG. 20). Best immune response in terms of IgG, IgA titer and serum neutralizing antibody titer was observed with 5 µg antigen+500 µg aluminium hydroxide formulation (FIG. 20).

Example 14: Stability of Inactivated Rotavirus Antigen

Rotavirus inactivated by heat at 49° C. for 4 days are purified, dialyzed and concentrated in TNC buffer. Sorbitol was added as a stabilizer to a final concentration of 10% and the antigen was aliquoted and stored at –20° C. Samples were taken at regular interval and total protein concentration was quantified by using a Pierce@ BCA Protein Assay (Thermo Scientific, USA). The inactivated antigen was found to be stable for 8 months at –20° C. with minimum loss of total protein (Table 10).

TABLE 10

Stability of inactivated rotavirus antigen at –20° C.

| | 0 day | 1 month | 2 months | 3 months | 4 months | 5 months | 6 months | 7 months | 8 months |
|---|---|---|---|---|---|---|---|---|---|
| IRV concentration | 0.7 mg/ml | 0.72 mg/ml | 0.69 mg/ml | 0.65 mg/ml | 0.67 mg/ml | 0.68 mg/ml | 0.65 mg/ml | 0.67 mg/ml | 0.64 mg/ml |

Example 15: Bi-Valent Vaccine Formulation and Potency Testing of Inactivated Rotavirus Antigen and Norovirus VLPs in the Combination Vaccine Rotavirus antigen was also co formulated with norovirus VLP and immunogenicity of the dual vaccine candidate was evaluated in Balb/C mice. Method for norovirus VLP production has been described above. 5 µg of rotavirus antigen inactivated by heat at 49° C. for four days was co-formulated with 10 µg norovirus VLPs and 500 µg aluminium hydroxide. The groups of mice used for the potency and immune interference testing are summarized in Table 11.

TABLE 11

Groups of mice for potency and immune interference testing of a bi-valent vaccine formulation

| Group | Vaccine formulation |
|---|---|
| Placebo (Alum) | 500 µg aluminium hydroxide/dose |
| IRV + Alum | 5 µg RV Antigen + 500 µg aluminium hydroxide/dose |
| NoV VLPs + Alum | 10 µg NoV VLPs + 500 µg aluminium hydroxide/dose |
| IRV + NoV VLPs + Alum | 5 µg RV Antigen + 10 µg NoV VLPs + 500 µg aluminium hydroxide/dose |

Figure 23:
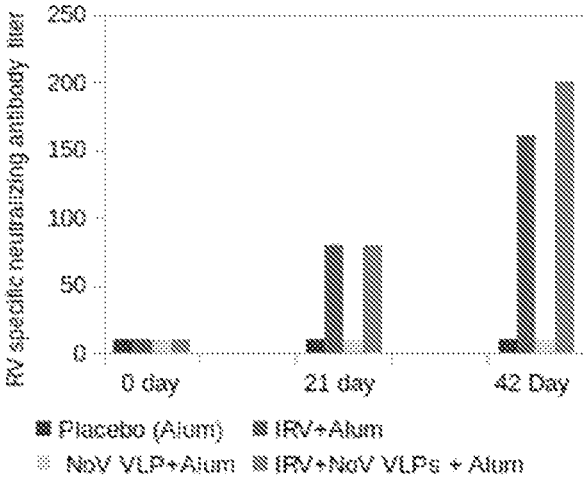
Figure 23:
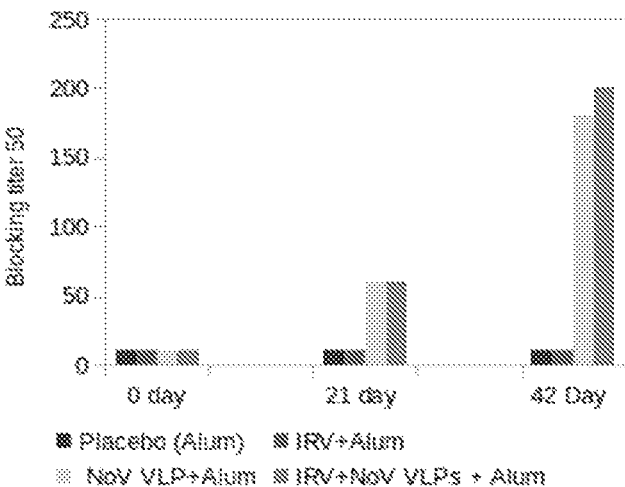

Mice in a group of 5 were immunized intramuscularly with two doses at three weeks interval. Blood was collected one day before each immunization and final bleed was taken on day 42. Serum was separated and assayed for rotavirus specific as well as norovirus specific immune response. Serum IgG, IgA and neutralizing antibody response were measured separately for both the antigen by previously described methods. FIGS. 21(*a*) and (*b*) demonstrated RV specific and NoV-VLP specific IgG response respectively in the bi-valent vaccine formulation. Similarly FIG. 22 (*a*) and (*b*) represented IgA response and FIG. 23 (*a*) and (*b*) represented neutralizing antibody titer against rotavirus and NoV-VLPs respectively. Immune response for each antigen was comparable when tested alone or in the bi-valent formulation. This showed that in bi-valent vaccine formulation one antigen did not interfere with immune response of the other antigen.

REFERENCE

Lindesmith L C, Debbink K, Swanstrom J, Vinje J, Costantini V, et al. (2012) Monoclonal antibody-based antigenic mapping of norovirus GII.4-2002. J Virol 86: 873-883.

I claim:

1. An immunogenic composition comprising:
   (a) a norovirus antigen comprising virus-like particles (VLPs) derived from norovirus capsid proteins,
   (b) inactivated rotavirus, and
   (c) a pharmaceutically acceptable carrier,
   wherein said composition is formulated as a single combined vaccine for prophylaxis and eliciting an immune response against rotavirus and norovirus infections.

2. The immunogenic composition as claimed in claim 1, wherein the norovirus antigen comprises VLPs that are applicable to protection against any genotype/strains/genetic variants of norovirus.

3. The immunogenic composition as claimed in claim 2, wherein the norovirus antigen is monovalent or bivalent or trivalent belonging to the same genogroup or different genogroup.

4. The immunogenic composition as claimed in claim 2, wherein the norovirus VLPs are derived from either expression of only VP1 protein or by co-expression of VP1 and VP2.

5. The immunogenic composition as claimed in claim 4, wherein an expression system selected from the group consisting of yeast cells, bacterial cells, insect cells and mammalian cells is used to express the VP1 and/or VP2.

6. The immunogenic composition as claimed in claim 5, wherein the expression system is the yeast *Pichia pastoris.*

7. The immunogenic composition as claimed in claim 5, wherein the VLP is concentrated and purified from cell supernatant by one or more methods selected from i) ultrafiltration through 100 kD-1000 kD membrane, ii) ultracentrifugation and density gradient centrifugation, and iii) column chromatography selected from gel filtration, ion exchange chromatography, hydrophobic interaction chromatography, and affinity matrix chromatography, or a combination thereof.

8. The immunogenic composition as claimed in claim 1, wherein the norovirus antigen is derived from any genotype of genogroup GI and GII.

9. The immunogenic composition as claimed in claim 8, wherein the norovirus antigen is derived from the group consisting of GII.4 strains.

10. The immunogenic composition as claimed in claim 9, wherein the norovirus antigen is derived from a single isolate or a chimera from different isolates of GII.4.

11. The immunogenic composition as claimed in claim 1, wherein the composition comprises i) purified norovirus VLPs and ii) 50 mM phosphate buffer, pH 7, and the composition is stable for 6 months at 4° C.

12. The immunogenic composition as claimed in claim 11, wherein the purified norovirus VLPs are present in the composition at a concentration ranging from 0.1 μg to 50 μg and the composition is formulated with or without an adjuvant.

13. The immunogenic composition as claimed in claim 12, wherein the adjuvant is selected from the group consisting of i) aluminum salts comprising aluminum hydroxide, aluminum phosphate, aluminum sulphate phosphate; ii) inulin; iii) algammulin which is a combination of inulin and aluminium hydroxide; iv) monophosphoryl lipid A (MPLA); v) CpG oligonucleotide; and vi) aluminum hydroxide with MPLA, or a combination thereof.

14. The immunogenic composition as claimed in claim 12, wherein the composition elicits a protective immune response against norovirus in mammals.

15. The immunogenic composition as claimed in claim 12, wherein the composition is administered as a single dose, two doses, or more than two doses.

16. The immunogenic composition as claimed in claim 12, wherein the composition elicits both a Th1 and Th2 immune response against norovirus.

17. The immunogenic composition as claimed in claim 1, wherein the composition is formulated with or without adjuvants.

18. The immunogenic composition as claimed in claim 1, wherein the composition provides immunity against rotavirus selected from human or animal rotavirus of group A, B, C, D, E, F and G.

19. The immunogenic composition as claimed in claim 18, wherein the rotavirus is derived from a live attenuated human rotavirus.

20. The immunogenic composition as claimed in claim 1, wherein the rotavirus in the formulation is purified and inactivated rotavirus.

21. The immunogenic composition as claimed in claim 20, wherein the rotavirus is inactivated by heat either before or after purification of the virus, wherein the virus is incubated at a temperature ranging from 42° C.-60° C., wherein incubation time range is from 30 minutes to 10 days to render the virus incapable of infection and replication.

22. The immunogenic composition as claimed in claim 21, wherein the inactivated rotavirus preparation comprises an amount of intact viral proteins VP1, VP2 and VP6 which are similar to the amount of native viral proteins VP1, VP2 and VP6 present in the starting preparation.

23. The immunogenic composition as claimed in claim 20, wherein the rotavirus is inactivated by chemical means either before or after purification of the virus.

24. The immunogenic composition as claimed in claim 23, wherein the rotavirus is inactivated by a technique selected from i) exposure to formalin at a concentration ranging from 1:1000 (formalin: virus, v/v) to 1:4000 (formalin: virus, v/v) at temperature 25° C.-37° C. for 3-10 days; and ii) exposure to hydrogen peroxide at a concentration ranging from 0.05% to 3% at 4° C. to 25° C. for a period of 4-48 hours.

25. The immunogenic composition as claimed in claim 20, wherein the rotavirus is inactivated by a combination of heat and chemical means either before or after purification of the virus; wherein the means comprise temperature ranging from 40° C.-55° C. in presence of formalin at a concentration ranges from 1:5000 (formalin: virus, v/v) to 1:50000 (formalin: virus, v/v) for a period of 2-24 hrs.

26. The immunogenic composition as claimed in claim 20, wherein the rotavirus is concentrated and purified by methods selected from i) ultrafiltration through 100 kD-1000 kD membrane, ii) ultracentrifugation and density gradient centrifugation, and iii) column chromatography selected from gel filtration, ion exchange chromatography, hydrophobic interaction chromatography, and affinity matrix chromatography, or a combination thereof.

27. The immunogenic composition as claimed in claim 20, wherein the inactivation is confirmed by a method with a sensitivity to detect 0.1 FFU/ml live rotavirus.

28. The immunogenic composition as claimed in claim 20 in a stable liquid vaccine formulation, wherein the stable liquid vaccine formulation comprises i) purified and inactivated rotavirus antigen, ii) TNC buffer (10 mM Tris, 140 mM NaCl, 10 mM $CaCl_2$), and iii) sugar concentration in the range of 0.1% to 10%, wherein the sugar is selected from lactose, maltose, sucrose, glucose, trehalose, and sorbitol, or a combination thereof.

29. The immunogenic composition as claimed in claim 28, wherein the liquid formulation is stable at −20° C. for 8 months.

30. The immunogenic composition as claimed in claim 29, wherein the rotavirus is at a concentration ranging from 0.1 μg to 100 μg and formulated with or without an adjuvant.

31. The immunogenic composition as claimed in claim 30, wherein the adjuvant is selected from the group consisting of i) aluminum salts comprising aluminum hydroxide, aluminum phosphate, aluminum sulphate phosphate; ii) inulin; iii) algammulin which is a combination of inulin and aluminium hydroxide; iv) monophosphoryl lipid A (MPLA); v) CpG oligonucleotide; and vi) aluminum hydroxide with MPL.

32. The immunogenic composition as claimed in claim 30, wherein the composition elicits a protective immune response against rotavirus in mammals.

33. The immunogenic composition as claimed in claim 30, wherein the composition is administered as single dose, two doses, or more than two doses.

34. The immunogenic composition as claimed in claim 30, wherein the composition elicits both a Th1 and Th2 immune response against rotavirus.

35. A method of preparing the immunogenic composition of claim 1, comprising: mixing the norovirus antigen and rotavirus in predetermined ratios; adding the pharmaceutically acceptable carrier; and formulating the mixture into a vaccine composition.

36. The immunogenic composition as claimed in claim 1, wherein the composition is capable of eliciting an immune response against rotavirus and norovirus infections when formulated with or without an adjuvants from other pathogens.

37. The immunogenic composition as claimed in claim 36, wherein the adjuvant is selected from the group consisting of i) aluminum salts comprising aluminum hydroxide, aluminum phosphate, aluminum sulphate phosphate; ii) inulin; iii) algammulin which is a combination of inulin and aluminium hydroxide; iv) monophosphoryl lipid A (MPLA); v) CpG oligonucleotide; and vi) aluminum hydroxide with MPL.

38. The immunogenic composition as claimed in claim 1, wherein the composition is administered as single dose, two doses, or more than two doses.

39. The immunogenic composition as claimed in claim 1, wherein the composition comprises rotavirus and norovirus antigens in a combination vaccine that elicits protective immune response in mammals against each of the viruses without immune-interference.

40. A method of eliciting a protective immune response in mammals including humans comprising administering the immunogenic composition as claimed in claim 1 by a route selected from the group consisting of intradermal, subcutaneous, intramuscular, intravenous, oral, and intranasal routes.

* * * * *